United States Patent
Dunseath et al.

(10) Patent No.: US 7,715,894 B2
(45) Date of Patent: May 11, 2010

(54) APPARATUS AND METHOD FOR ACQUIRING A SIGNAL

(75) Inventors: William James Ross Dunseath, Charlottesville, VA (US); Tor Andrew Alden, Basking Ridge, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/084,716

(22) PCT Filed: Nov. 7, 2006

(86) PCT No.: PCT/EP2006/010674

§ 371 (c)(1),
(2), (4) Date: May 8, 2008

(87) PCT Pub. No.: WO2007/054273

PCT Pub. Date: May 18, 2007

(65) Prior Publication Data
US 2009/0099473 A1    Apr. 16, 2009

(51) Int. Cl.
*A61B 5/04* (2006.01)
*A61B 5/0476* (2006.01)

(52) U.S. Cl. .............. 600/383; 600/544; 600/545; 600/382; 600/372

(58) Field of Classification Search .......... 600/544–545
See application file for complete search history.

(56) References Cited

U.S. PATENT DOCUMENTS

| | | | | | |
|---|---|---|---|---|---|
| 4,537,200 | A | * | 8/1985 | Widrow | 600/509 |
| 4,777,954 | A | * | 10/1988 | Keusch et al. | 600/392 |
| 5,178,143 | A | * | 1/1993 | Kwak et al. | 600/397 |
| 5,601,091 | A | * | 2/1997 | Dolphin | 600/559 |
| 6,052,614 | A | * | 4/2000 | Morris et al. | 600/509 |
| 6,256,531 | B1 | * | 7/2001 | Ilmoniemi et al. | 600/544 |
| 6,488,617 | B1 | * | 12/2002 | Katz | 600/26 |
| 2004/0030258 | A1 | * | 2/2004 | Williams et al. | 600/544 |

FOREIGN PATENT DOCUMENTS

DE    9201475 U  *  4/1992

* cited by examiner

*Primary Examiner*—Robert L Nasser
*Assistant Examiner*—Michael D'Angelo
(74) *Attorney, Agent, or Firm*—Ellen Plotkin

(57) ABSTRACT

An electrode cap for obtaining EPM signals from a head of a subject, the cap comprising: (i) an insulating layer (33) for positioning adjacent to the head of the subject; (ii) an electrically conductive layer (29) comprising ionic conduction means, situated above the insulating layer so that in use, it is separated from the head of the subject by the insulating layer; (iii) a plurality of measurement signal electrodes (13) extending through the electrically conductive layer and the insulating layer for contacting the head of the subject, the measurement signal electrodes being electrically insulated from the electrically conductive layer; and (iv) at least one reference node (53, 55) electrically connected to the electrically conductive layer.

38 Claims, 9 Drawing Sheets

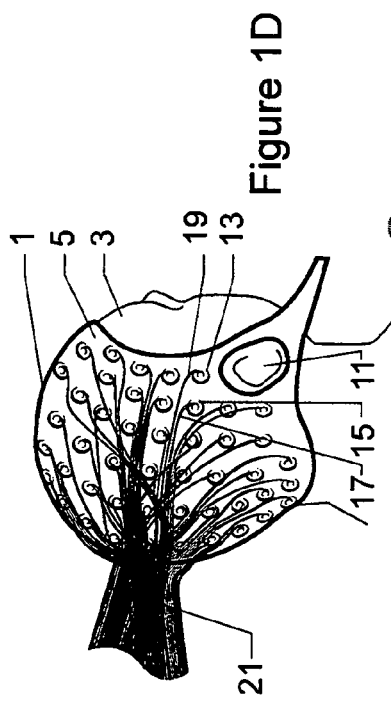
Figure 1D
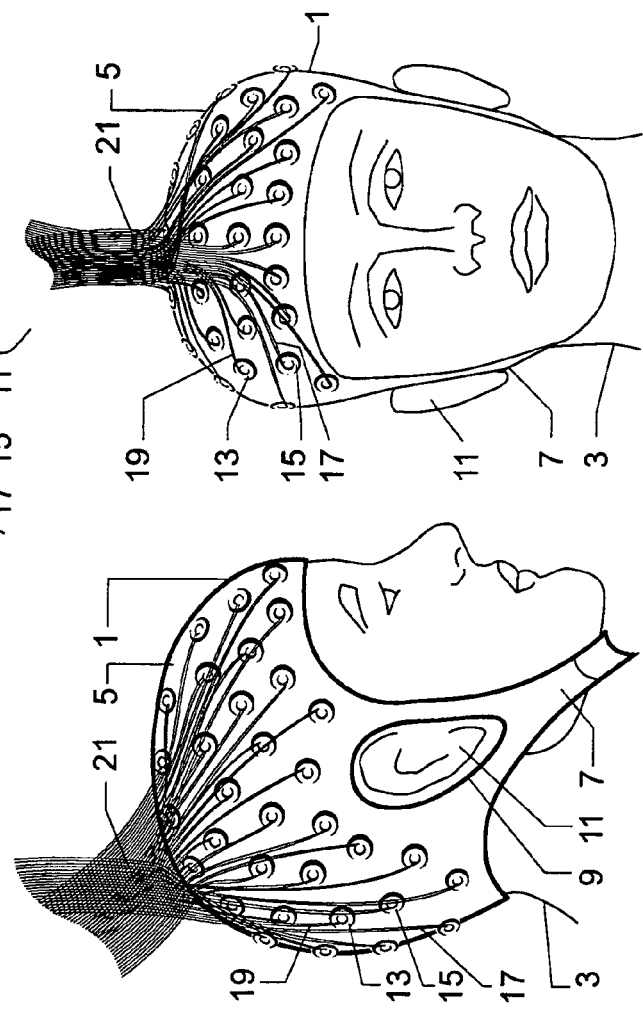
Figure 1C
Figure 1B
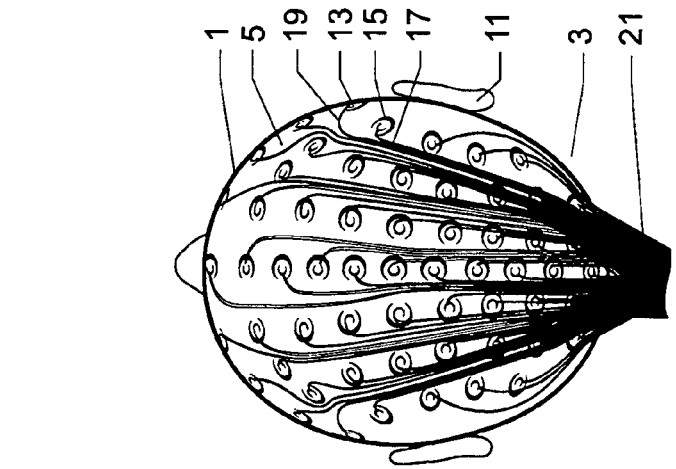
Figure 1A

APPARATUS AND METHOD FOR ACQUIRING A SIGNAL

FIELD OF THE INVENTION

This present invention relates to an electronic apparatus and method for obtaining an electroencephalography (EEG) or analogous signal, especially when subject to one or more sources of interference. More particularly, it relates to an electrode support or cap, and use thereof.

BACKGROUND OF THE INVENTION

An EEG signal is derived from electrodes placed on the head of a subject and is conveyed via leads to processing circuitry and monitoring equipment. The EEG signals themselves are relatively weak. A similar situation applies to other kinds of electrophysiological measurement (EPM). These techniques are therefore prone to interference arising from the subject, e.g. eye blink artefacts or from the surrounding environment, e.g. electrical mains interference. An EEG signal obtained from a scalp electrode is in the range typically of 10 µV to 100 µV at an impedance of around 500Ω to 50 KΩ.

EEG has traditionally been used for investigations into brain activity. It may, for example, be employed to investigate abnormal brain activity in disease states such as epilepsy or in certain psychiatric abnormalities.

There is also an interest in obtaining EEG measurements in combination with techniques which involve use of a strong magnetic field and sometimes also radiofrequency (rf) fields. One such technique is functional magnetic resonance imaging (fMRI). Such magnetic and rf fields represent yet another source of interference for the EEG measurements. The large magnetic and radio frequency fields produced by MRI machines easily swamp the EEG signal with induced noise on the signal wire. Further, switching of the MRI magnetic gradients causes extraneous pulses in the EEG signal.

The fMRI technique is widely used in both medical and non-medical imaging to obtain a spatial image of "slices" through the brain. In the medical context, MRI is used to identify lesions such as areas of restricted blood flow or tumours. Outside the medical field, fMRI has, for example, been a useful tool in cognitive neuroscience for investigating brain response to various external stimuli. However, there are other techniques which involve use of a strong magnetic field and may also be used in combination with EEG, as will be mentioned further hereinbelow. They also give rise to noise problems.

There have been many proposals for reducing interference signals in EEG. For example, U.S. Pat. No. 5,445,162 proposes a system using electrodes and wiring designed to minimise noise in EEG signals when obtained in combination with use of fMRI. The EEG recording equipment is located outside the MRI room to minimise interference.

U.S. Pat. No. 5,513,649 proposes a system for removing contaminants from EEG recordings. It proposes that an adaptive filter is used to estimate the contaminants in the measured EEG data and then subtracts them from the primary signal to obtain the corrected EEG data.

WO-A-03/073929 discusses the potential problems associated with concurrent fMRI and EEG measurements, namely noise induced in the EEG signal by the rf and magnetic fields (as mentioned above) and the disruption to the fMRI measurement by introduction of ferromagnetic material in the EEG electrodes, into the bore of the fMRI machine. This reference comments upon possibilities for alleviating these problems. One is to dispense with ferromagnetic materials in the EEG electrodes and to use an alternative such as carbon fibre. Another is to rearrange the EEG leads to minimise interference with the rf field.

The aforementioned WO-A-03/073929 also recognises safety problems inherent in deploying EEG equipment inside a pulsed rf field, e.g. due to induced currents. Solutions to these problems have included raising the impedance of the EEG detection circuit by means of resistors or by using different electrode systems or different electrode materials, or by incorporating a fibre optic link in the line between the electrodes and the circuit. The reference proposes that a better method of avoiding such hazards is to incorporate an amplifier within the electrode structure.

WO-A-02/13689 describes a method of reducing interference in EEG, ECG and EMG, especially in combination with MRI, whereby pairs of electrodes are connected to differential amplifiers. An interference signal is obtained by synchronisation of measurement signals with a timing signal which initiates digitisation of the signals. Subtraction of the interference is then effected digitally.

A system wherein separate EEG measurement signal electrodes and so-called reference electrodes are employed is disclosed in International Patent Application No. PCT/EP2005/006126, unpublished at the priority filing date of this application. The reference electrodes are electrically isolated from the subject. Signals from the individual reference electrodes are subtracted from those on respective measurement signal electrodes to remove interference. One preferred means of supporting the measurement signal electrodes and reference electrodes as disclosed in this reference, is in the form of an electrode support or cap. The reference electrodes comprise connections or "nodes", electrically connected to a continuous conductive web or mesh which is electrically isolated from the subject by an insulating layer. This conductive layer may be formed from carbon-loaded fabrics, foam or yarn or a silver coated polymer such as nylon.

The present invention, in one aspect, is concerned with an alternative design of electrode cap which is optimised for use with the noise cancellation system disclosed in PCT/EP2005/006126 but which embodies several novel and inventive features. In another aspect, it relates to an electrode cap design for improving contact with the subject and minimising movement of the electrodes relative to the head of the subject.

It may be noted that there have been a number of prior proposals for electrode support caps for electrodes used in EEG measurement. EP-A-0 541 393 discloses such a support in the form of a headpiece which comprises elastic strips on which the electrodes are supported.

WO-A-00/27279 discloses a stretchable elastic cap on which are supported, soft rubber electrode holders.

US-A-2002/0007128 discloses a system for combined EEG monitoring with simultaneous transcranial magnetic stimulation (TMS). Disclosed in this reference is an electrode system using a conductive plastic electrode cup with an integral silver epoxy coated electrode to ensure that the impedance of the electrode system as a whole is reduced to be equivalent to that of a typical metal electrode.

An electrode cap in which sensing electrodes are replaced with electrical devices adapted both for measuring electric voltage or current, and also for applying an electric current or voltage is described in U.S. Pat. No. 6,594,521.

SUMMARY OF THE INVENTION

A first aspect of the present invention provides an electrode cap for obtaining EPM signals from a head of a subject, the cap comprising:

(i) an insulating layer for positioning adjacent to the head of the subject;
(ii) an electrically conductive layer situated above the insulating layer so that in use, it is separated from the head of the subject by the insulating layer, the electrical conductivity of the electrically conductive layer being predominantly due to ionic conductive means;
(iii) a plurality of measurement signal electrodes extending through the electrically conductive layer and the insulating layer for contacting the head of the subject, the measurement signal electrodes being electrically insulated from the electrically conductive layer; and
(iv) at least one reference node electrically connected to the electrically conductive layer.

In a preferred embodiment of the first aspect of the present invention, a plurality of reference nodes is electrically connected to the electrically conductive layer, preferably spaced apart over the cap, most preferably in positions adjacent to respective measurement signal electrodes.

In an electrode cap according to the second aspect of the present invention, any one or more, e.g. all of the electrodes may be of the kind of the measurement signal electrodes of the first aspect of the present invention.

It should also be noted that in a variant of the first aspect of the present invention, the measurement signal electrodes may be individually placed on or adhered to the head of the subject and then an electrode cap having only features (i), (ii) and (iv) being placed over those electrodes. Thus, a variant of the first aspect of the invention provides an electrode cap for obtaining EPM signals from a head of a subject, the cap comprising:
(i) an insulating layer for positioning adjacent to the head of the subject;
(ii) an electrically conductive layer situated above the insulating layer so that in use, it is separated from the head of the subject by the insulating layer; the electrical conductivity of the electrically conductive layer being predominantly due to ionic conductive means; and
(iii) at least one, preferably a plurality of reference nodes electrically connected to the electrically conductive layer.

Any reference hereinafter to an electrode cap according to the first aspect of the invention also includes a reference to the above defined variant of the first aspect of the invention, unless the context forbids. Therefore, references hereinafter to a plurality of reference nodes are to be taken as also including the possibility of a single reference node unless the context forbids.

The first aspect of the present invention may also be expressed in terms of a method of effecting one or more reference connections to an electrode cap for obtaining EPM signals from the head of a subject, by providing an electrically conductive layer situated above an insulating layer, the insulating layer being for positioning adjacent to the head of a subject, the electrically conductive layer being situated above the insulating layer so that in use, it is separated from the head of the subject by the insulating layer, the electrical conductivity of the electrically conductive layer being predominantly due to ionic conductive means, at least one reference node being electrically connected to the electrically conductive layer.

A second aspect of the present invention provides an electrode cap for obtaining EPM signals from the head of a subject, the cap comprising an electrode support means for at least partly covering a head of a subject, a plurality of electrodes being supported on said electrode support means to allow said electrodes to contact the head and bladder means for securing said electrodes relative to the head.

The second aspect of the present invention may also be expressed as a method for securing measurement electrodes relative to the head of a subject from which EPM signals are obtained, by means of bladder means.

A variant of the second aspect of the present invention provides an electrode cap according to the second aspect of the invention as defined above but wherein the electrode support means carries only a single electrode, for example a needle-type electrode. Thus any reference hereinafter to an electrode cap according to the second aspect of the invention also includes a reference to this variant, unless the context forbids. Therefore references hereinafter to a plurality of electrodes supported by the electrode support means of the cap of the second aspect of the invention is to be taken also as including the possibility of a single such electrode, unless the context forbids.

The electrode cap according to the first aspect of the present invention utilises an electrically conductive layer, the electrical conductivity of which is predominantly due to ionic conductive means. The ionic conductive means relies on at least one ionic species to enable electrical current to pass therethrough. Preferably, the at least one ionic species is dissolved and/or dispersed in a continuous medium such as a liquid, paste or gel. Preferably, the continuous medium is substantially aqueous, preferably such that part of the electrically conductive means which is not an ionic species comprises at least 50% by weight, more preferably at least 80% by weight of water. However, optionally it may comprise at least some non-aqueous material such as one or more non-aqueous ingredients selected from water-miscible and water-immiscible non-aqueous materials, which may be of a substantially organic nature, for example selected from aromatic and aliphatic organic compounds, especially aromatic and aliphatic liquid organic materials, for example hydrocarbons, and surfactants. Such non-aqueous materials may be liquids, pastes, gels or solids. It is also possible for the continuous medium to be substantially entirely non-aqueous.

The ionic species may comprise one or more materials existing as associated or partly or substantially wholly dissociated ions, i.e. having at least one anion and at least one cation. Preferably the ionic species is selected from one or more salts, especially selected from one or more salts selected from organic salts and inorganic salts. In any event, water soluble salts, especially those water soluble to at least a reasonable extent at 25° C. and atmospheric pressure, are preferred. The inorganic salts are the most preferred, such as water soluble alkali metal salts or alkali earth metal salts, most preferably one or more alkali metal salts selected from sodium, potassium and lithium inorganic salts, for example chlorides, sulphates and nitrates of the alkali metals, although additionally or alternatively, one or more salts of these metals with one or more organic anions such as citrate, lactate, maleate, malonate, oxalate and the like may be employed.

Where the continuous medium is a viscous liquid, paste or gel, it may also comprise one or more thickening agents. Polymeric thickening agents are particularly preferred, for example synthetic polymers or copolymers derived from one or more monomer units such as maleate, acrylate, styrene, pyrrolidone and imidazoline containing monomers. Natural or naturally derived thickening agents may also additionally or alternatively be employed, such as polysaccharide gums, for example guar gum, xanthan gum, karaya gum, konjak, starches and the like, as well as gelatine, alginate etc. In principle, there is no constraint on the identity of such thickening agents, since the only purpose is to increase the viscosity of any liquid component of the continuous medium.

The continuous medium may be solid but when it is a viscous liquid, paste or gel, it may for example have a viscosity greater than 5,000, especially more than 25,000 mPas, when measured at a sheer rate of 23 s$^{-1}$. However, the continuous medium may also be a gel which although deformable when provided as a sheet material, is relatively hard. A particularly preferred example of such a gel which is electrically conductive is one such as described in EP-A-1 100 556. Such materials comprise an aqueous plasticizer and a copolymer of two hydrophilic unsaturated water-soluble monomers such as 2-acrylamido-2-methylpropanesulphonic acid or a salt thereof and a salt of acrylic acid (3-sulphopropyl) ester. These materials are sometimes referred to as "conductive adhesive hydrogels" and are commercially available from First Water Ltd.

The resistivity of the electrically conductive medium is preferably from 0.1 ohm-cm to 1000 ohm-cm, more preferably from 1 ohm-cm to 350 ohm-cm. The electrically conductive layer will preferably present an impedance when measured at any of the reference nodes (connections) of typically from 100 ohms to 10,000 ohms, preferably from 500 ohms to 1,500 ohms. This impedance will typically have a negligible inductive reactance and will consist mainly of pure resistance and capacitive reactance. The capacitive reactance will be determined primarily by the capacitance appearing in the interface between the scalp of the subject and the measurement signal electrode, which is a multi-layered construction consisting of electrode material, electrode gel, and the various layers of skin and sweat pores in the scalp itself. The combination of resistive and capacitive elements appearing in the measurement electrode interface to the scalp forms a complex impedance network with a response that is frequency dependent. An extremely simple model of this interface may be constructed with the series combination of a resistor and capacitor in parallel with a resistor. With this model, the capacitance for a typical measurement electrode interface as considered herein would fall between 0.1 μF and 10 μF.

The primary aim of the first aspect of the present invention is to match the overall impedance of the reference nodes as closely as possible to that of the measurement electrodes (averaged over all measurement electrodes and reference nodes, respectively). Typically, the average impedance of the reference nodes should be within ±200%, more preferably ±100% of the average impedance of the measurement electrodes. This optimises the cap design to work most efficiently with the noise cancellation circuitry which is described and claimed in our unpublished copending International Patent Application No. PCT/EP2005/006126.

The conductivity of the electrically conductive layer in the electrode cap according to the first aspect of the present invention is predominantly due to the ionic conductive means. Ionic conductive means are different forms of conductive materials deriving their conductivity from, say, aqueous or aqueous-based solutions of salts such as alkali metal or alkaline earth metal salts, especially inorganic salts (typically sodium chloride or potassium chloride) or even dispersions of metal particles or film or carbon particles of film. The ionic means must be the predominant cause of electrical conductivity within the electrically conductive layer. However, optionally, up to 50% of this conductivity may also be contributed by conductive means other than ionic conductive means although preferably at least 75%, more preferably at least 90%, especially more than 95% and in the ideal situation, substantially all of the conductivity of the electrically conductive layer is due to the ionic conductive means.

To enhance impedance matching with the skin the relative permittivity of the skin is preferably from 1,000 to 70,000 at least one frequency in the range of from 10 Hz to 1,000 Hz The second aspect of the present invention relates to an electrode cap which comprises a bladder means (bladder) for securing the measurement electrodes relative the head. This has the advantages of urging the measurement electrodes to be in good electrical contact with the head and/or preventing unwanted movement of the electrodes and preferably also the leads during the measurement operation. The bladder may also provide cushioning for the head. Such an electrode cap may also comprise the electrically conductive layer of the first aspect of the invention but the bladder means may also be used in any other design of electrode cap in which a support layer supports a plurality of electrodes. The support layer may be a discrete member separate from the bladder or it may be integral therewith.

In one class of embodiment in the second aspect of the invention, the bladder is inflatable. Inflation of the bladder causes the securing of the electrodes relative to the subject's head. This inflation may be caused by injection of a fluid, liquid or gas, but preferably air into the bladder. The inflation means is preferably provided integral to the cap. This can allow the bladder to be inflated or deflated at will or maintained in the inflated state.

In another class of embodiment of electrode cap according to the second aspect of the present invention, the bladder secures the electrodes against the head of the subject when it is deflated, or rather caused to be in a reduced pressure or semi-vacuum or vacuum state. In that case, means for withdrawing fluid, preferably air, (reducing the pressure) from inside the bladder, is preferably provided integral with the bladder. In this class of embodiment, the inside of the bladder should contain solid articles such as beads or granules, which, when the inside of the bladder is reduced in pressure or evacuated, mould their bulk shape to that of the head. Such an embodiment may be considered as a "vacuum beanbag".

A third class of embodiments of the second aspect of the present invention comprises means for creating a "memory polymer" e.g. in the form of a polymer foam inside the bladder. This may comprise a pair of rupturable bags inside the bladder. Each bag would contain a respective reactant. When squeezed, the bags would rupture allowing the reactants to mix and generate the resultant foam which would mould itself to the shape of the subject's head whilst curing. A suitable system to be embodied in this way is commercially available as RediFoam™ available ex Medtec Inc. The hardened polymer would then be specific to the individual subject and the bladder may therefore be disposable. Another way of achieving the same thing would be to inject hardening foam into the bladder when the cap is in place on the subject.

The bladder may be in the form of a generally cap-shaped layer of may have holes (preferably generally round or elongate) or leadthroughs for the connections to the electrodes. It may be shaped so as to comprise a plurality of separated fingers, the spaces allowing room for the electrodes and leads. The fingers may, for example, extend upwardly from a continuous (e.g. generally circular) part of the bladder, both the continuous and finger regions being inflatable or deflatable.

Throughout this specification, wherever there is reference to one layer being above or below another layer, those two layers may be in direct contact or separated from each other by one or more intermediate layers.

An electrode cap according to any aspect of the invention is preferably shaped and dimensioned to fit, in use, snugly over at least 50%, more preferably at least 90% of the area of the average adult cranium, i.e. over much (preferably at least 50%, more preferably at least 80%) of the area of the parietal bone and at least 50% (most preferably the upper 50%) more preferably at least 80% of the area of the frontal bone. It is preferably formed so as to be, in use, concave on the electrode (i.e. measurement signal electrode in the case of the first aspect of the invention) face, side or surface and convex on its upper face, side or surface.

The invention also extends to any electronic apparatus according to either aspect of the invention and an electronic circuit comprising:
  (a) a plurality of measurement signal inputs, each connected to a respective one of the measurement signal electrodes; and
  (b) at least one, preferably a plurality of reference signal line inputs, each connected to a respective one or more of the reference nodes;

electronic apparatus further comprising subtraction means for subtracting an interference signal from each respective reference signal input from an interference signal from a corresponding measurement signal input or from each respective measurement signal line in the measurement signal line group in that measurement input in a group of measurement signal inputs.

Each measurement signal electrode may be associated with its own reference signal node or the measurement signal electrodes may be grouped into one or more groups each comprising a plurality of measurement signal electrodes each having its own at least one associated reference signal node. A combination of these arrangements is also possible. In one example, there may be only one reference signal node.

It is intended that in use, the electrically conductive layer of an electrode cap according to the first aspect of the present invention will not be in direct electrical contact with the subject but the measurement signal electrodes will be in direct electrical contact with the subject. As used herein, "direct electrical contact" preferably means a contact resistance of 10K ohms or less, preferably 1K ohms or less and "not in direct electrical contact" is to be construed accordingly. In some preferred embodiments, "direct electrical contact" as used herein preferably means a contact impedance or a resistance of 2.5K ohms, more preferably 1K ohms or less, and most preferably 100 ohms or less and "not in direct electrical contact" is to be construed accordingly.

Each electrode site on any suitable cap structure may for example have four wires—two for the signal loop and two for the reference loop—arriving as two twisted pairs twisted around each other. One wire connects to the body electrode; one wire connects to the electrically conductive layer next to the electrode; one wire proceeds across the cap to the body ground electrode; and one wire proceeds across the cap to the electrically conductive layer ground connection. A multichannel arrangement would comprise a plurality (n) of such sites.

As used herein, the term "group" in relation to electrode groups preferably means two or more. In some applications, typically 8 measurement signal electrodes are appropriate but for others, up to 32 or even 64 may be desirable.

Preferably a compensation signal line and most preferably, also an associated reference line is also provided. As a generality, a compensation signal on the compensation signal line, derived from a separate compensation line electrode, is used to reduce interference in the or each measurement signal. Preferably, the signal on the compensation signal line is processed in a compensation signal processing unit to produce a plurality of compensation signal components. The compensation signal components are respectively used to reduce interference in respective interference reduction modules which process the respective measurement signal or signals preferably after subtraction of all or part of the corresponding reference signal or signals.

A compensation signal is preferably derived from a separate compensation signal electrode (similar or identical to a measurement signal electrode) connected to a neutral (relatively non-responsive) part of the subject.

Thus, in one kind of arrangement, the or each measurement signal is derived via a respective measurement signal line connected to its own measurement signal electrode and for each such measurement signal line, there is a corresponding reference signal line in close proximity therewith for a substantial part of their mutual lengths (or one or more group(s) of measurement signal lines may share a single reference signal line in close proximity in the same way). Each such reference signal line is connected to a respective reference node or connection point which in use, is positioned close to its corresponding measurement signal electrode. Preferably, the compensation signal line (when utilised) is also provided with a corresponding reference signal line connected to a reference node or connection point, situated close to the compensation signal electrode. Preferably, each reference signal is at least partially subtracted from the corresponding measurement signal, or signals in the case of a shared reference signal line, (or the compensation signal, as the case may be), for example with the respective primary signal unit (or compensation signal unit). Preferably, the compensation signal line has its own reference line in close physical proximity therewith along a substantial part of their mutual lengths.

For at least some measurement signal lines and/or the compensation signal line, more than one additional reference line may be provided, connected to the same reference electrode or its own respective reference electrode. As stated above, it is also possible for one or more groups of measurement signal lines to share one or more associated reference signal lines.

In another alternative, corresponding ground connections/ground lines are provided for each signal, compensation, and reference connections or electrodes and lines, or each signal line/reference line pair and the compensation line/reference line pair shares a respective single common ground line. A ground line may also be provided for the compensation signal line and any accompanying reference line. In a particularly preferred embodiment, substantially all such ground lines are connected to a shared single ground electrode.

The interference reduction may optionally employ adaptive noise cancellation, preferably in real time, in which the amount of interference to be removed may be determined dynamically and varied over time.

Preferably, the interference reduction modules in each primary signal processing unit are arranged in series. Preferably, in each primary signal processing unit, separate interference reduction modules are provided for reducing at least two of magnetic switching interference, mains power interference, eye blink artefact interference and ballistocardiogram interference.

In an EEG measurement employing an embodiment of the present invention, any electrodes to the human or animal skin (e.g. scalp) may be dry or "wet" (i.e. employing an electrically conductive gel or paste).

Any circuit element or method step independently may be implemented by analog or digital means.

At least one compensation signal line may be provided for connection to a compensation signal electrode. The compensation signal electrode is preferably located on a subject in a "neutral" position (e.g. in the case of EEG, on or near an ear).

The resultant at least one compensation signal, delivered via the compensation signal line(s) may be used to at least partially reduce interference on the (measurement) signal line or lines, e.g. by a subtractive process. The compensation signal line is preferably associated with its own reference line which is preferably in close physical proximity thereto along a substantial part of their mutual lengths and is connected to a reference electrode (node) associated with the compensation signal electrode.

This embodiment may find particular use in electrophysiological measurement systems such as EEG, which when combined with MRI such as fMRI, gives rise to ballistocardiogram (BCG) interference.

In preferred realisations of the present invention, a "reference loop" is used for subtracting at least some interference signals induced by external fields into a circuit loop. In preferred embodiments described hereinbelow, this circuit loop is formed by the connection between the reference electrode(s) and electronic amplification circuitry. In such arrangements, a simplified version of the reference loop is described for use in multi-channel EPM recordings, such as EEG recordings in order to reduce noise voltages induced by the magnetic fields generated in a functional magnetic resonance imaging device (fMRI). In addition, an embodiment of a complete circuit means is described for acquiring simultaneous EPM in the MRI or fMRI environment, with minimal interference to the EPM and fMRI. EPM signals such as EEG signals can still have large interference components if used also without fMRI or the like, e.g. generated by electric motors in the vicinity. The present invention is also useful in such applications, reducing or removing the need for screening of the noise source and/or data acquisition circuitry.

In order to achieve EPM data acquisition, concurrent with fMRI, the EPM data acquisition circuitry must reject interference caused by external (to the body) electric and magnetic fields. The main sources of interference are low frequency electric and magnetic fields from the AC power mains (commonly 50 or 60 Hz), switched magnetic fields from fMRI with switching rates ranging down to approximately 500 Hz, and radio frequency (rf) electromagnetic fields from fMRI at 60 MHz or higher. Another source of interference is ballistocardiogram noise due to pulsing of circulatory blood in the magnetic field. In addition, the large static magnetic field of the MRI scanner causes interference voltage to be induced in EPM signal lines whenever movement of the electrodes or lead wires occurs. At least two of these are reduced as separate interference components in accordance with the first and second aspects of the present invention.

A single measurement signal line can be connected to a respective separate measurement signal electrode. A reference line may be connected to a single reference node or to a respective separate reference node of a plurality of reference nodes or any other arrangement involving multiple reference nodes.

Each signal line (or group of signal lines) may therefore be associated with a corresponding one of the reference lines to be in close proximity for a substantial part of their lengths, so that each respective signal line and associated reference line constitutes a respective signal line (or signal line group)/reference line pair. The subtraction means is then arranged to subtract an interference signal on each reference line from the interference signal on its associated signal line (or each signal line of the respective group) in the pair, thereby enhancing the desired signal on that signal line.

Also desirable is provision of one or more ground lines. Any signal line/reference line pair may share a common ground line, preferably in close physical proximity with both, or each signal line and reference line may be provided with its own ground line, preferably in close physical proximity therewith. A combination of such arrangements is also possible (one or more shared ground lines for some signal/reference line pairs and one or more individual ground lines for any one or more others). All ground lines may be connected to a common ground electrode or to individual respective ground electrodes, or any other arrangements involving multiple ground electrodes. Preferably, the or each ground electrode is in direct (low resistance) contact with the subject (e.g. the skin of the head or scalp in the case of EEG), as described further hereinbelow. In an especially preferred class of embodiments, a plurality of measurement signal lines has each connected to a respective measurement signal electrode. Each measurement signal line (or group of measurement signal lines) has its own associated reference signal line connected to a respective reference signal electrode (node). A separate ground electrode is connected to a ground line and a separate compensation signal electrode is connected to a compensation signal line. The compensation signal line and ground line each have a respective associated reference line connected to a dedicated additional respective reference node.

Where an individual line or lines (measurement signal, compensation signal, reference signal or ground) is or are connected to its, or their, own dedicated electrode (signal, reference, or ground, respectively), that electrode may be embodied as two or more electrode entities with the reference line or lines being connected thereto in parallel. The terms "electrode" and "node" (see below) are to be interpreted as encompassing these possibilities, except where explicitly stated to the contrary or where the context forbids.

The or each measurement signal line, compensation signal line and/or ground line, as the case may be, may be in close physical proximity for a substantial part of the length thereof, with a respective reference line, a respective ground line, or both, preferably twisted together therewith.

Preferably, signal and any ground electrodes are in direct electrical connection with the subject (usually the head, or head/neck region when the EPM is EEG, e.g. mainly to the scalp). This preferably means an individual electrode contact resistance of less than 2.5K ohms, more preferably less than 1K ohms.

For the avoidance of doubt, in any description of electronic circuitry suitable for use with an electrode cap in accordance with the first aspect of the present invention, reference to subtraction of an interference signal or component means any attenuation of interference on a signal line by deriving an interference signal from a corresponding reference line and using it to diminish the interference signal on the signal line. Arithmetic subtractions as well as other operations are included within this term. The definition includes substantial total elimination of the interference signal but also covers at least some diminution of the interference signal from the signal line.

In the electronic circuitry which may be employed, the subtraction means preferably comprises a differential amplifier with inverting and non-inverting inputs connected to signal line(s) and reference line(s) respectively.

Each signal line/reference line pair may be shielded, for example by a metallic sheathing which suitably may be connected to a ground connection.

The subtraction means may also comprise one or more common mode chokes associated with the respective signal line/reference line pairs, the windings of each such common mode choke being connected to a respective one of the signal line and the reference line. The subtraction means preferably also comprises low pass filter means, especially a seventh order low pass filter, an exemplary embodiment of which comprises a 0.05° Equiripple-type filter.

When used in combination with MRI or fMRI, the apparatus of any aspect of the present invention may be deployed in the MRI room itself, although recording may be conducted outside that room. The apparatus of any aspect of the present invention may be substantially totally electrically wired, i.e. not require any optical or wireless link, although the latter are also possible.

One or more preferred embodiments of the present invention provide for substantially simultaneous data acquisition and read-out, thus providing minimal lag between data acquisition and data availability, as may otherwise arise due to post-processing, for example.

An electrode cap according to the present invention may be employed for any electrophysiological measurement (EPM) alone or in combination with MRI, fMRI or TMS. It can also be used to reduce interference on signals obtained from magnetoencephalography (MEG). MEG is a technique analogous to EEG which instead of using an electrode on the surface of the head, uses an array of sensors to measure change in magnetic fields outside the skull generated by neuronal activity.

The present invention is useful in the application of medical or quasi-medical EPM measurements, or academic, commercial or forensic applications.

For the avoidance of doubt, any class or example of any preferred or optional feature described herein, may be combined with any one or more other class or example of any preferred or optional feature, unless they are presented as mutually exclusive alternatives. In the appended claims, the features of any dependent claim may be used in combination with those of any one or more other dependent claim (unless presented as mutually exclusive alternatives) regardless of whether they are dependent on the same independent claim and regardless of the category of independent claim(s) on which they are dependent. Any electrode cap in accordance with the first aspect of the present invention may optionally also be in accordance with the second aspect of the present invention.

The present invention will now be explained in more detail by way of the following description of preferred embodiments, and with reference to the accompanying drawings, in which:—

DESCRIPTION OF THE DRAWINGS

FIG. 1A shows a plan view of a first embodiment of an electrode cap according to the present invention;

FIG. 1B shows a side elevation of the electrode cap of the embodiment of FIG. 1A;

FIG. 1C shows a front elevation of an electrode cap of the embodiment shown in FIGS. 1A and 1B;

FIG. 1D shows a general perspective view from the rear of the electrode cap of the embodiment depicted in FIGS. 1A-1C;

DESCRIPTION OF PREFERRED EMBODIMENTS

Figure 2:
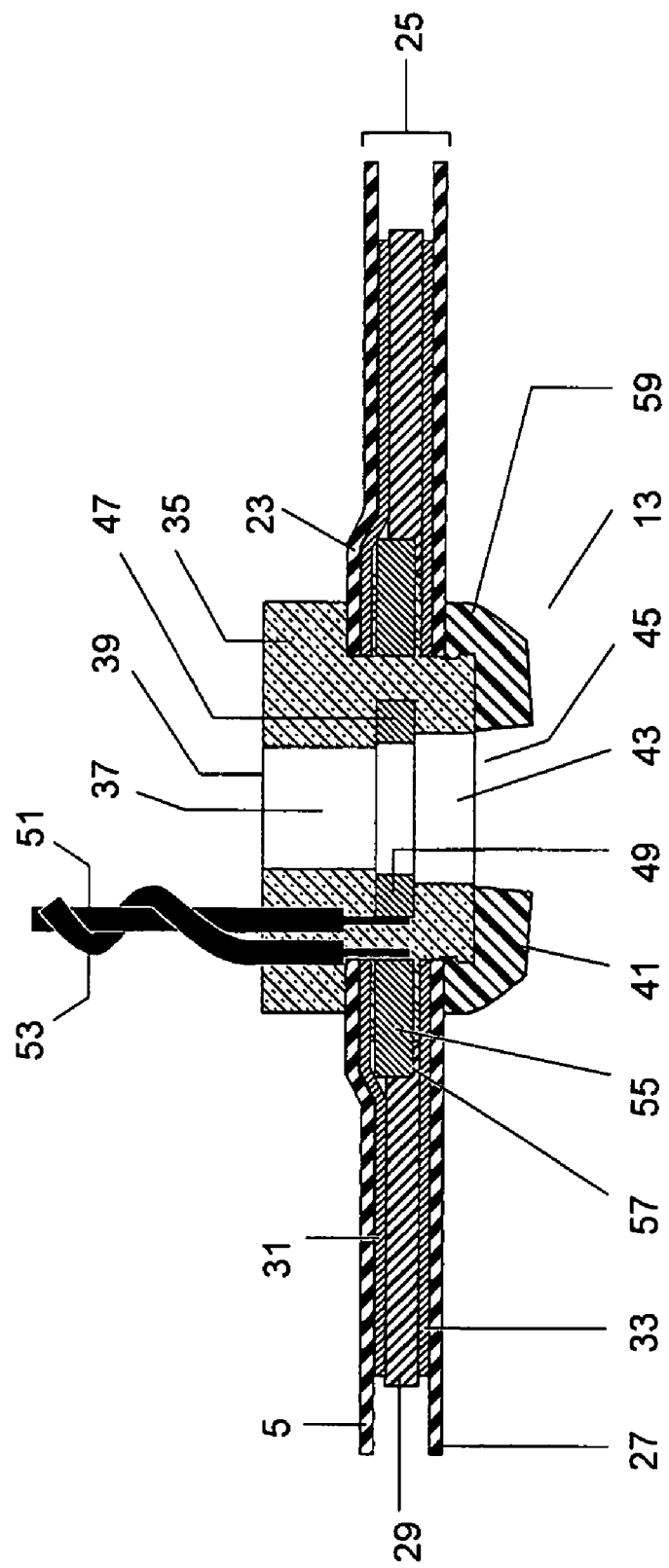
FIG. 2 shows a cross-section through an electrode as used in the embodiment of FIGS. 1A-1D.
Figure 3B:
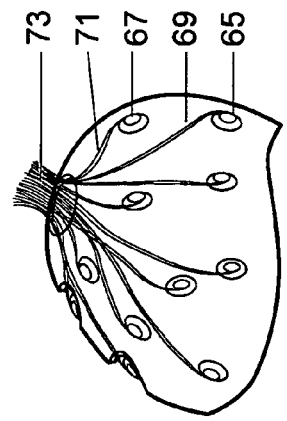
FIG. 3B shows a perspective view of an electrode support in a cap of the second embodiment of electrode cap depicted in FIG. 3A.
Figure 3C:
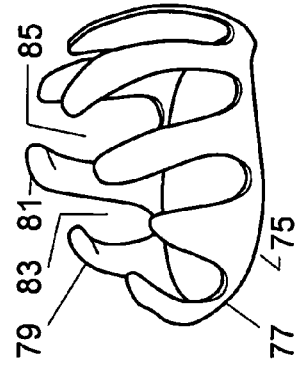
FIG. 3C shows a perspective view of an intermediate bladder for use in the electrode cap of the embodiment of FIGS. 3A and 3B.
Figure 3D:
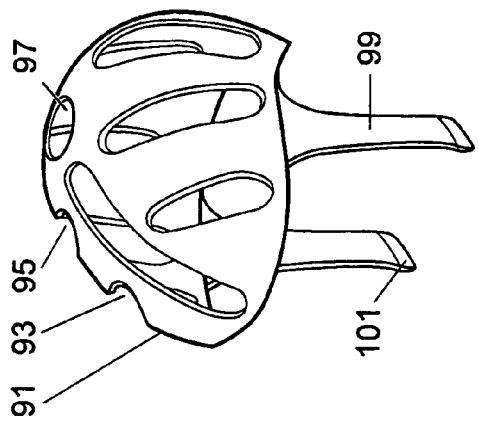
FIG. 3D shows a rigid outer helmet of the second embodiment of electrode cap depicted in FIGS. 3A-3C.
Figure 3A:
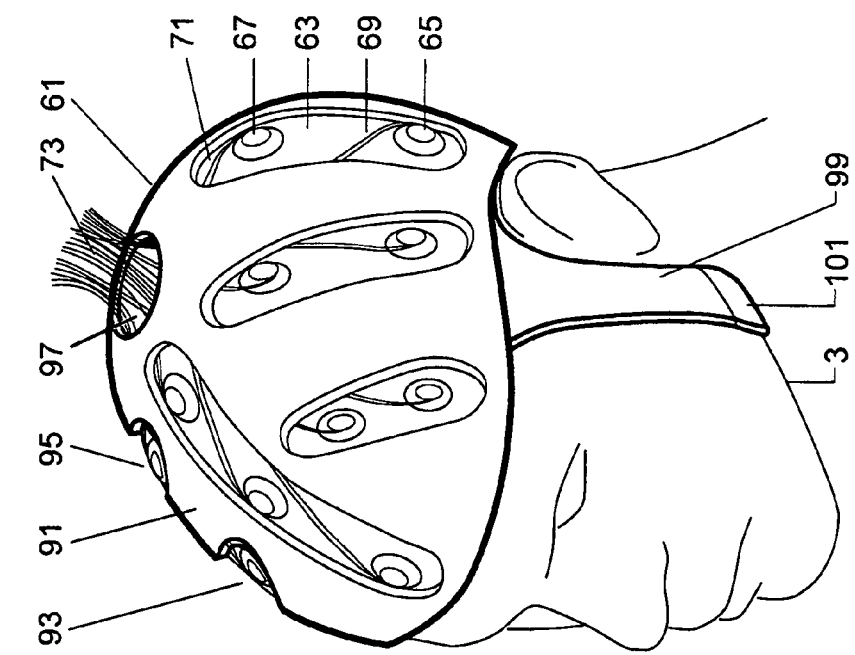
FIG. 3A shows a general front perspective view of a second embodiment of an electrode cap according to the present invention.

FIGS. 1A-1D show various views of a first embodiment of an electrode cap 1 on the head of a subject 3. The cap is in the form of a stretchable one piece item comprising a waterproof outer membrane 5 of Lycra™ or another stretchable fabric, with a removable and washable internal layer (not shown in these Figures).

The cap is retained on the head of the subject 3 by means of an integral chin strap 7 and covers practically the whole of the cranium, but is provided with holes 9 etc. to leave the ears 11 etc of the subject 3 exposed.

The cap is provided with a plurality of electrodes 13, 15 etc as will be explained in more detail hereinbelow. Each electrode 13, 15 etc is provided with electrical lead connections 17, 19 etc. The electrical leads 17, 19 etc are joined together in a lead bundle 21, to be connected to electronic circuitry, as will also be explained in more detail hereinbelow.

The construction of the individual electrodes 13, 15 etc can be seen in FIG. 2 which shows in cross-section, the details of one particular electrode 13.

This electrode leads through a hole 23 formed in a laminar structure 25 which comprises the upper (outermost during wear) waterproof Lycra™ layer 5 and a lowermost Lycra™ layer 27. Sandwiched between these upper and lower layers 5, 27 is an electrically conductive gel layer 29, which is extensive throughout the cap, except where interrupted by penetration of the electrodes 13, 15 etc. Above and below the conductive gel layer 29, are thin pliable upper and lower film layers 31, 33 etc, made of an electrically insulating plastics material, situated respectively below and above the upper and lower Lycra™ layers 5, 27.

The electrode itself consists of a plastics grommet 35 having a central bore 37 therethrough, open at its upper (outermost) end 39 and its lowermost end 41. The lower portion 43 of the central bore 37 widens into a well 45. In use, when the lower end 41 of the bore 37 is in direct contact with the subject's head, the bore 37 is filled with a conductive gel. This may or may not be the same kind of conductive gel as that in the electrically conductive gel layer 29 but in any event, is chosen to ensure good electrical contact with the subject. This gel is not shown in FIG. 2.

Electrical contact with the gel for contacting the subject is made by means of an interior annular carbon member 47 held in a recess 49 within the plastics grommet member 35 and surrounding the central bore 37. The annular member 47 could also be made of carbon loaded polymer. Exterior electrical connection to this annular member 47 is made by virtue of an external connection wire 51 in electrical contact therewith.

A reference connection node is constituted by electrical connection of a second externally connecting wire 53 with an outer annular carbon member 55, concentric with, radially separated from, and surrounding the interior annular carbon member 57, so as not to be in electrical contact therewith. Again, the outer annular member 55 could also comprise carbon loaded polymer. This exterior conductive carbon annular member 55 is in electrical contact with the electrically conductive gel layer 29 and is held in place between the insulating plastics layers 31, 33 by means of adhesive 57.

To ensure minimisation of leakage of the conductive gel inserted into central bore 37, lower end 59 of the plastics member 35, protruding below the lower Lycra™ layer 27, may be provided with a Neoprene™ annular sealing member (not shown).

The method of manufacturing the cap shown in FIG. 1A-1D will now be briefly described. First, a "head form" (manufacturing support) is created with protrusions to extend through the relevant layers, to create the holes for the electrodes. This is not shown in the drawings.

The annular sealing members 59 are placed over the protrusions. A pre-sewn Lycra™ inner layer 27 is then placed over the annular members 59. Next, the gel layer 29, sandwiched between protective insulating layers 31, 33 is placed over the other Lycra™ layer 27. The upper Lycra™ layer 5 is then placed over that structure and then the plastics insert 35 with electrically connecting carbon discs 47, 55 is snapped into place. The perimeter of the cap (periphery of the various layers) is then sealed.

FIGS. 3A-3D show various fragmentary and whole views of a second embodiment of an electrode cap 61 according to the present invention. The complete cap as shown on the head of a subject 3 can be seen in FIG. 3A.

The cap of this embodiment comprises an inner soft cap member 63 on which is supported a plurality of electrodes 65, 67 etc, having respective electrical leads 69, 71. These electrodes and leads are of the same structure as depicted in FIG. 2. The cap member 63 also contains a conductive gel layer, as shown in FIG. 2. The leads from each electrode are brought together to form a lead bundle 73. This can be seen in FIG. 3B. Over the inner or lower electrode support cap member 63 fits an inflatable air bladder 75. The lower periphery 77 of the bladder 75 is continuous but extending upwardly therefrom, is a plurality of inflatable fingers 79, 81 etc. These fingers are separated by gaps 83, 85 etc. The bladder 75 is inflated or deflated by pump means not shown in FIG. 3. The gaps 83, 85 are positioned such that when the bladder 75 is placed over the electrode supporting cap member 63, the electrodes 65, 67 etc are situated in these gaps. An outer rigid helmet shell 91 fits over the bladder 75, when in place over the electrode support cap member 63. In a variation of this embodiment, the outer shell may be formed of a softer material.

The helmet shell 91 is provided with a plurality of elongate slots 93, 95 etc. In practice, these elongate slots are positioned such as to correspond to and overlie, the gaps 83, 85 etc between the fingers 79, 81. The electrodes 65, 67 are thereby exposed. The electrical leads 69, 71 etc run in the space between the electrode cap member 63 and the helmet shell 91, along and inside the bladder finger gaps 83, 85 etc, to come together in the electrical bundle 73 which exits through a top hole 97 in the helmet shell 91. The whole assembly is held in place on the subject 3 by means of chin strap 99, attached to the helmet shell 91. The strap 99 is provided with a Velcro™ fastening 101.

Figure 4C:
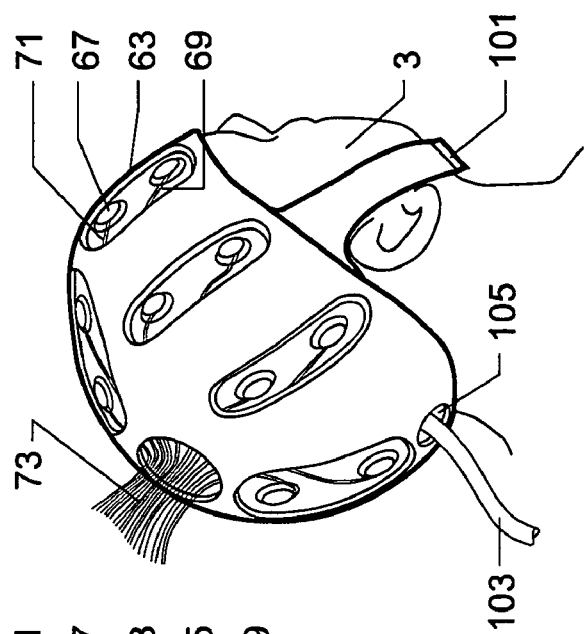
FIGS. 4A-4C depict the method of assembly and wearing of the second embodiment of the electrode cap as depicted in FIGS. 3A-3D.
Figure 4B:
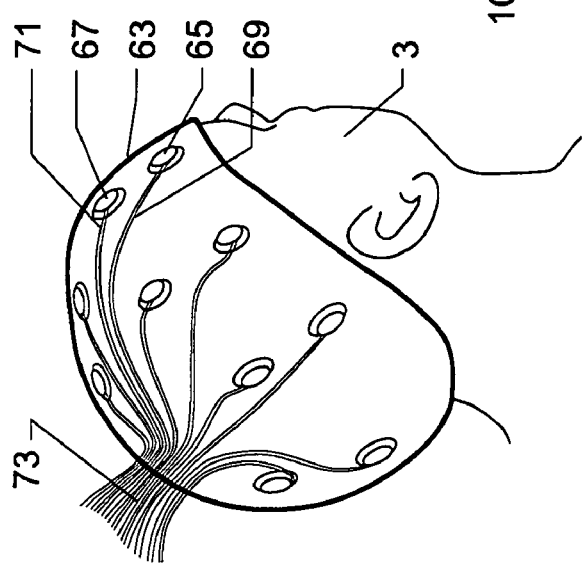
Figure 4A:
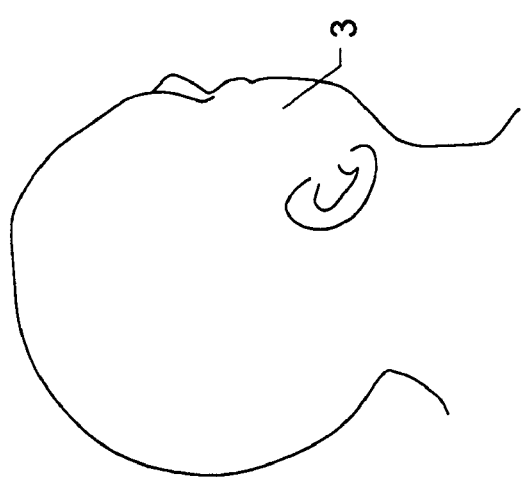

The cap is fitted in place on the subject 3, as depicted sequentially in FIGS. 4A-4C.

As shown in FIG. 4A, the subject 3 is prepared to receive the cap. First, the electrode support cap member 63 is placed over the subject's head (FIG. 4B). Then, as shown in FIG. 4C, the bladder 75 (not shown) and then the helmet shell 91 is placed over the entire assembly. It can be seen in FIG. 4C, that the bladder 75 is connected to an air tube 103 which exits through a hole 105 in the rear of the helmet shell 91. This air tube is connected to an air bulb (not shown) with valve means, enabling air to enter into and inflate the bladder, and to be retained therein, until released to effect deflation.

In use, when inflated, the bladder ensures a positive pressure is exerted on the electrode support cap member 63 to force it against the head of the subject, minimising the risk of movement between the electrodes and the scalp.

Figure 5C:
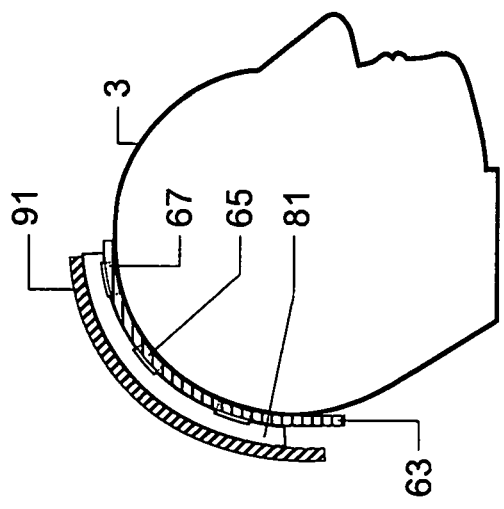
FIG. 5C is a cross-section corresponding to that of FIG. 5A, but with the bladder inflated.
Figure 5D:
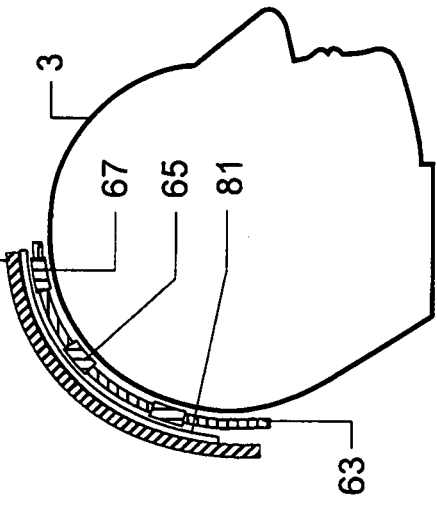
FIG. 5D is a cross-section corresponding to that of FIG. 5B, but with the bladder inflated.
Figure 5A:
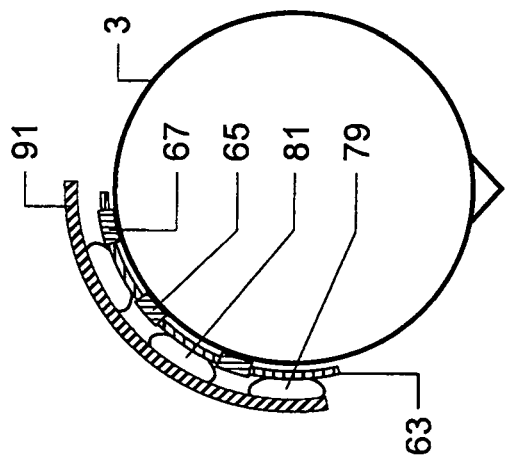
FIG. 5A shows a partial cross-section of the electrode cap depicted in FIGS. 3 and 4 in a horizontal cut through the head of a subject, the bladder being deflated.
Figure 5B:
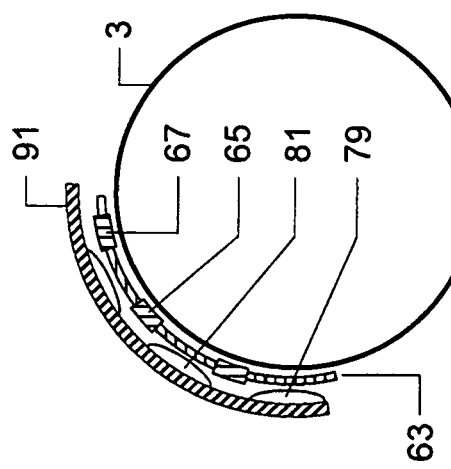
FIG. 5B shows a cross-section corresponding to that of FIG. 5A, but vertically through the head of the subject.

FIGS. 5A-5D show a cross-section through the entire assembly of FIGS. 3A-3D and 4A-4C, as seen from various angles. For convenience, the head of the subject 3 is shown only in outline. FIG. 5A and FIG. 5B show the fingers 79, 81 etc deflated, in plan view (FIG. 5A) and side elevation (FIG. 5B).

Similarly, FIGS. 5C and 5D show respective plan and side elevation views, with fingers 79, 81 etc inflated.

In the embodiments of FIGS. 1 and 2, and 3 to 5, respectively, the resistivity of the reference layer was 60 Ωcm. The average impedance of the reference nodes was 900 ohms when measured at 10 Hz.

Figure 6:
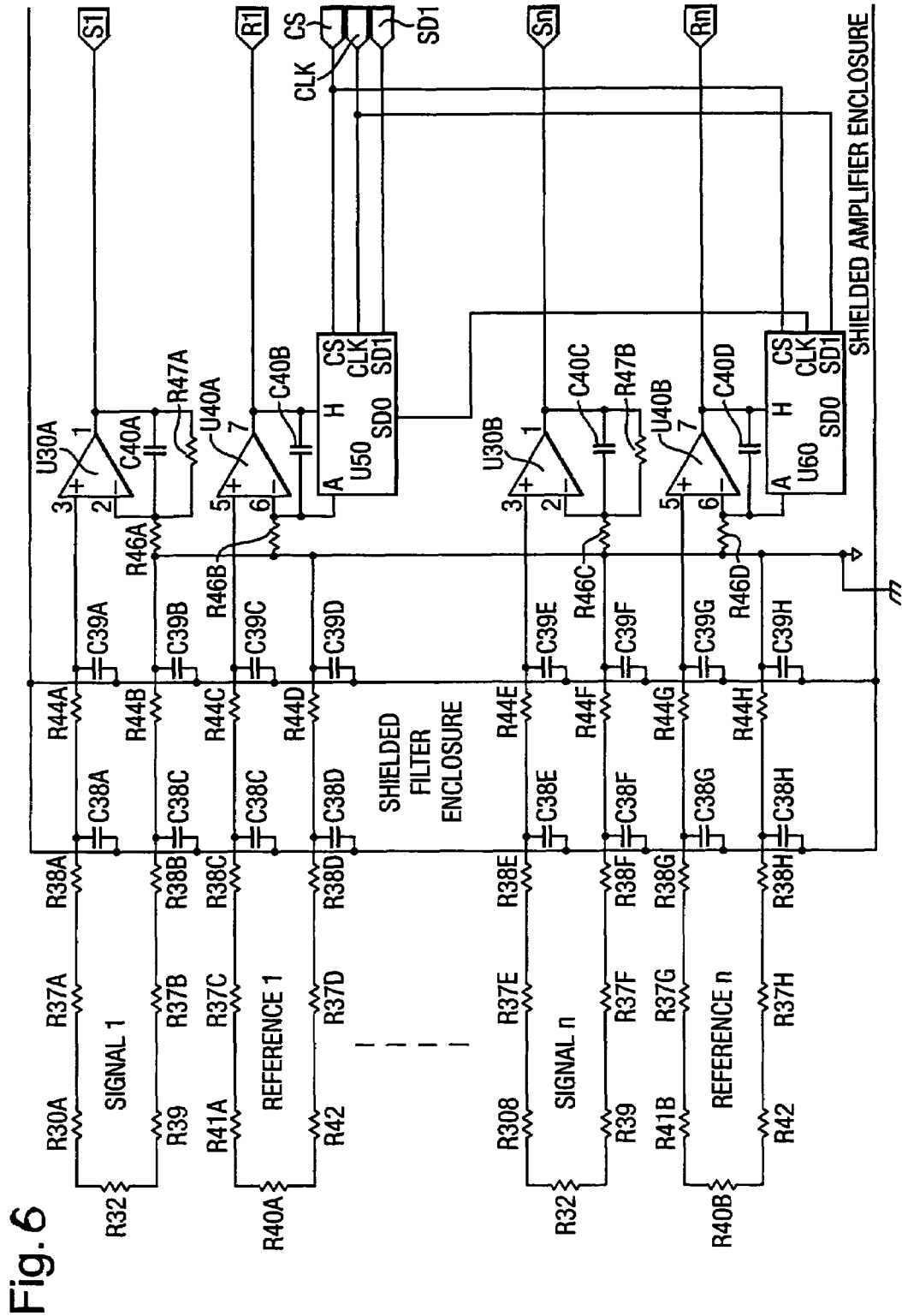
FIG. 6 is a first example of a front end of circuitry for use with the electrode caps of the embodiments shown in FIGS. 1-5.

FIG. 6 shows the front end circuitry of a signal processing circuit which may be connected to an electrode cap of either of the preceding embodiments.

Referring to FIG. 6, there are n measurement channels, where n could range from 2 to 1024 but is typically 32 or 64. For convenience, only the $1^{st}$ and n'th channels are actually shown in the drawing. Each measurement channel comprises a signal line and a reference line connected to respective measurement signal electrodes and reference nodes of the electrode cap. A ground line (not shown) is connected to an electrode constructed like a measurement signal electrode positioned on the cap at the nape of the neck. That ground line is connected to ground. Another such electrode also having a corresponding reference node is positioned on the cap in the earlobe position (close to earlobe) and constitutes a compensation signal electrode.

Respective associated measurement signal lines and reference lines are twisted together. The ground line is bundled with the bundle of measurement signal line/reference line pairs.

Thus, as shown, there are n measurement channels (1 to n) of identical construction such as is shown for measurement channel 1. As the n channels are of identical construction, only Channel 1 will be described in detail below. Channel 1 comprises signal line pair designated "Signal 1" and reference line pair "Reference 1". As depicted, the signal line of "Signal 1", is connected to the scalp for EEG via a signal or measurement electrode with an impedance represented by resistor R31A, preferably having an electrode impedance of around 10K ohms or less. Other signal electrodes are denoted R30B etc. All body electrodes preferably are constructed of a resistive material such as carbon-loaded plastic, or the bare ends of carbon wire. Contact to the body is made via a conductive gel.

In a signal channel 1, outside a shielded filter enclosure, a number of resistors R30A, R32, R37A, R37B, R38A, R38B and R39 are connected in series. A first terminal of the resistor R32 is connected to a first terminal of the resistor R30A and the second terminal of the resistor R30A is connected to the first terminal of the resistor R37A, the second terminal of the further resistor R37A being connected to the first terminal of the resistor R38A. The second terminal of the resistor R32 is connected to the first terminal of the resistor R39 and the second terminal of the resistor R39 is connected to the first terminal of the resistor R37B, the second terminal of the resistor R37B being connected to the first terminal of the resistor R38B. In the reference channel 1, outside a shielded filter enclosure, a number of resistors R37C, R37D, R38C, R38D, R40A, R41A and R42 are connected in series. The first terminal of a first resistor R40A is connected to the first terminal of the resistor R41A, the second terminal of the resistor R41A being connected to the first terminal of the resistor R37C. The second terminal of the further resistor R37C is connected to the first terminal of the resistor R38C and the second terminal of the resistor R40A is connected to the first terminal of a resistor R42. The second terminal of the resistor R42 is connected to the first terminal of the resistor R37D and the second terminal of the resistor R37D is connected to the first terminal of the resistor R38D.

Similar connections exist for the other channel/reference pairs.

For channel 1 (and similarly for all signal channels), the wires represented by R37A and R37B are twisted together tightly to minimize the loop area formed by the wires and hence minimize induced magnetic field interference in the signal.

Thus, in measurement channel 1, R41A is a connection of a carbon wire to a conductive reference mesh that spans the surface of the head but is not in electrical contact with the body. R41A is located very close to R30A. R40A represents the impedance of the reference mesh. R42 is the connection from the mesh to the return wire for the reference loop, represented by R37D. R42 is located very close to R32. The wires for the reference loop (R37C and R37D) are twisted together tightly to minimize loop area, and the pair is twisted together with the R37A-R37B pair to match the paths followed by the loops.

Preferably the impedances of R30A and R41A are matched, as well as those of R32 with R40A, and R39 with R42. However, it is acceptable if only the sums of impedances R30A+R32+R39 and R41A+R40A+R42 are reasonably matched.

In the shielded filter enclosure, in the signal line the second terminal of the resistor R38A is connected to a capacitor C38A and also to the first terminal of a resistor R44A. The second terminal of the resistor R38B is connected to the first terminal of a capacitor C38B and also to a resistor R44B. The second terminals of the capacitors C38A and C38B are connected to the shielded filter enclosure.

The second terminal of the resistor R44A is connected to the first terminal of a capacitor C39A and also the non-inverting input of an operational amplifier U30A.

In the shielded filter enclosure, in the reference line the second terminal of the resistor R38C is connected to the first terminal of a capacitor C38C and to the first terminal of a resistor R44C. The second terminal of the resistor R38D is connected to the first terminal of a capacitor C38D and to the first terminal of a resistor R44D. The second terminals of the capacitors C38C and C38D are connected to the shielded filter enclosure.

In the shielded amplifier enclosure, in the signal line the second terminal of the resistor R44A is connected to the first terminal of a capacitor C39A. The second terminal of the resistor R44B is connected to the first terminal of a capacitor C39B and also to the first terminal of a resistor R46A. The first terminal of the resistor R46A is also connected to circuit ground. The second terminal of the resistor R46A is connected to the inverting input of the operational amplifier U30A and to the first terminal of a capacitor C40A as well as to the first terminal of a resistor R47A. The second terminal of the capacitor C40A and the second terminal of the resistor R47A are connected to the output of an operational amplifier U40A to provide the signal output S1.

The second terminal of the resistor R44C is connected to the first terminal of a capacitor C39C and to the non-inverting input of an operational amplifier U40A. The second terminal of the resistor R44D is connected to the first terminal of a capacitor C39D and to the first terminal of a resistor R46B as well as to circuit ground. The second terminal of the resistor R46B is connected to the inverting input of the operational amplifier U40A and to the first terminal of a capacitor C40B as well as to one resistive input of a digitally controlled potentiometer U50. The control signals, namely clock, chip select and SD1 are connected to the three digital inputs of the digitally controlled potentiometer U50. The second terminal of the capacitor C40B is connected to the output of the operational amplifier U40A and to the second terminal of the resistor chain of the digitally controlled potentiometer U50. As mentioned above, the second terminals of the capacitors C38A to C38D and C39A to C39D are connected to the shielded amplifier enclosure.

The output of the amplifier U40A is the reference output signal.

The signal appearing on the reference circuit is subtracted from the signal circuit. If impedances and wire pathways are well matched between signal and reference loops, the magnetically induced interference appearing in the signal circuit will be removed by subtraction of the reference signal.

Each resistor designated R32 represents the impedance of body tissue, typically 100 ohms, between signal and ground electrodes. Each resistor designated R39 represents the ground electrode, preferably 10K ohms or less, located typically at the top of the head or at the base of the neck. Similarly, each resistance R42 represents the corresponding ground electrode for the associated reference electrodes R41A, R41B etc. Resistors R37 (A through H) represent the resistance of the carbon wire connecting the electrode or reference loop to the electronic amplifiers, combined with the resistance of a patient safety resistor. A typical value for R37 is 6K ohms. The safety resistor typically is 5.1K ohms (range 5K to 15K ohms), preferably non-magnetic (such as Ohmite Macrochip™ SMD resistor), and is mounted in the electrode wire close (within 0.3 m) to the patient. Preferably, the safety resistors are mounted inside or immediately adjacent to their respective electrodes.

All of the components associated with the reference mesh and body electrodes may be considered impedances (i.e. having to greater or lesser degrees, resistive, inductive and capacitive components). Thus, except where indicated explicitly to the contrary or where the context does not permit, as used herein, all references to resistance may be regarded as including reference to impedance and "resistive" should be interpreted likewise.

The body electrodes (R30A-etc and R42) are composed of resistive elements at all frequencies and significant capacitive elements down to about 10 Hz. R32, the body tissue beneath the scalp, may be considered to be solely resistive below 100 Hz. R41A-etc in the reference mesh corresponds to R30A-etc, and R40A-etc in the reference mesh corresponds to R32, with the goal being to match these corresponding elements electrically, primarily in the frequency range for physiological signals of interest, 1-1000 Hz. Above that range the electronic filters take over for eliminating magnetic and rf noise. There are capacitive and inductive elements in the reference mesh that are significant at rf, and matching the impedances of the loops at rf is desirable. However, for matching purposes, the maximum tolerable range may be considered to be a DC resistance measured in a reference mesh loop of 50 to 50K ohms (measured at the point where the loop connects to the cable, i.e., in front of resistance R37). A preferred range would be an impedance of between 1K and 10K ohms measured in the reference loop at a frequency of 10 Hz. The body electrode impedances (at 10 Hz) are preferably lower than 10K ohms with a maximum of 20K ohms measured between the signal electrode and ground electrode.

Generally, there may be some level of electrical interconnection between the points of connection to the reference mesh, depending on the construction. If a continuous conductive fabric or foam is used, there is significant connection throughout the material, and R40A-etc are all connected by primarily resistive and capacitive elements. At the other end of the spectrum, if a lattice network is used, then conductive strings connect the various junctions where R41A-etc. meet R40A-etc. Thus, "reference electrode" is to be interpreted as encompassing the extremes and all possible intermediate forms of construction. The connections are again primarily resistive and capacitive, and can be every junction connected to every other junction at one extreme, or at the other extreme just nearest neighbouring junctions connected.

The nth channel is connected to a neutral location (close to areas of physiological signals of interest but without signal activity) such as behind the ear or on the earlobe for EEG, and has the same configuration (as the signal channels) of a signal loop paired with a matching reference loop. Thus, the n'th channel conveys a compensation signal whilst measurement signals are provided via channels 1 to (n–1). R32 serves as a common ground electrode to the body for all signal circuits, and similarly R42 is a common ground connection to the reference mesh for all the reference circuits. In the nth channel, the amplifiers corresponding to U30A and U30B are designated as U33A and U33B respectively and the digitally controlled potentiometer corresponding to U50 is designated as U60.

The patient cable consisting of all carbon wires twisted in pairs is approximately 2 to 5 meters in length and terminates at the shielded enclosure containing rf filters, analog amplifiers, filters, A/D converters and digital control circuitry. Filtering for rf interference is accomplished with two layers of filters separated by a five-sided shielded enclosure (labelled "Shielded Filter Enclosure" in FIG. 6). The first rf filter begins with resistors R38, 100 to 1K ohms, carbon or thick film composition. Capacitors C38 represent feedthrough capacitors of 1000 pF to 10,000 pF inserted into the wall of the shielded filter enclosure. Alternatively, capacitors C38 may be replaced by a filter connector such as Amphenol™ part number 21-474021-025 which has a pi filter configuration.

Resistors R44 begin the second rf filter (same values and types as R38), with feedthrough capacitors C39 (same values and types as C38) inserted into the wall of the shielded amplifier enclosure. Further rf filtering may be accomplished with the use of a 4-channel common mode choke for the four leads of each channel, and or the addition of a 100 to 1K ohm resistor followed by a 1 to 5 nF capacitor to ground in the leads to the non-inverting inputs of each preamplifier (pins 3 and 5 of U30 and U40 in FIG. 10), and or the insertion of a 100 to 500 pF capacitor between the inverting and non-inverting inputs of the preamplifiers.

Circuit power ground (common), denoted by the triangle symbol within the shielded amplifier enclosure near the bottom of FIG. 6, is preferably connected to the metallic shield enclosure in one location as shown in the Figure but the shield may also remain isolated from circuit ground. Although circuit power connections are not shown in the Figures, it is understood that the analog integrated circuit amplifiers and filter IC's, etc., are connected to bipolar power supplies of typically ±2.5 volts to ±10 volts, and digital modules are connected to +5 volts. Power is supplied preferably from batteries located within the shielded amplifier enclosure, but may also be supplied from an external power source (isolated medical grade power supply or batteries) if the power inputs are filtered for rf at the shield enclosure, using filters similar to those shown for the signal lines.

The preamplifiers (U30 and U40 in FIG. 6) are typically low noise, high input impedance dual operational amplifiers such as Analog Devices AD8620 or OP2177. On the signal side (U30A and U30B in FIG. 6) a gain of 2 (typical, range 1 to 4) is established by resistors R46 and R47, typically 33K ohms. On the reference side, variable gain is implemented by the use of a digitally controlled potentiometer (U50 and U60 in FIG. 10) in place of R47. This allows the dynamic adjustment of the reference signal gain under programmatic control for maximum interference reduction. Alternatively, R47 on the reference side may be a resistor matched to R47 on the signal side.

High resolution is necessary for precision matching of signal levels in the channels; Analog Devices™ AD7376 with 128 positions, or Analog Devices AD5231 with 1024 steps are examples of digital potentiometers that may be used for U50 and U60. In one example, an AD7376 of 100K ohms is used with R46 and R47 equal to 33K ohms. In this instance, the signal gain is 2 and the reference gain varies from 1 to approximately 4. In another example, an AD5231 of 50K ohms is used with R46 and R47 equal to 17K ohms. In this case the signal gain is again 2, and the reference gain varies from 1 to approximately 4, but the resolution of adjustment is greatly improved with 1024 steps instead of 128. In both cases, the control of the potentiometer is implemented via three digital control lines, labelled CS, CLK and SDI in FIG. 6. This method of control is desirable as it enables "daisy chaining" the digital potentiometers as shown in FIG. 6, which is advantageous for adjusting reference levels when large numbers of channels are used. Capacitors C40 reduce noise from the digital potentiometers when adjusting; they are used on the signal amplifiers to keep the bandwidths of the signal and reference amplifiers closely matched.

The CS, CLK and SDI inputs are the digital controls for the variable potentiometers U50 and U60.

Figure 7:
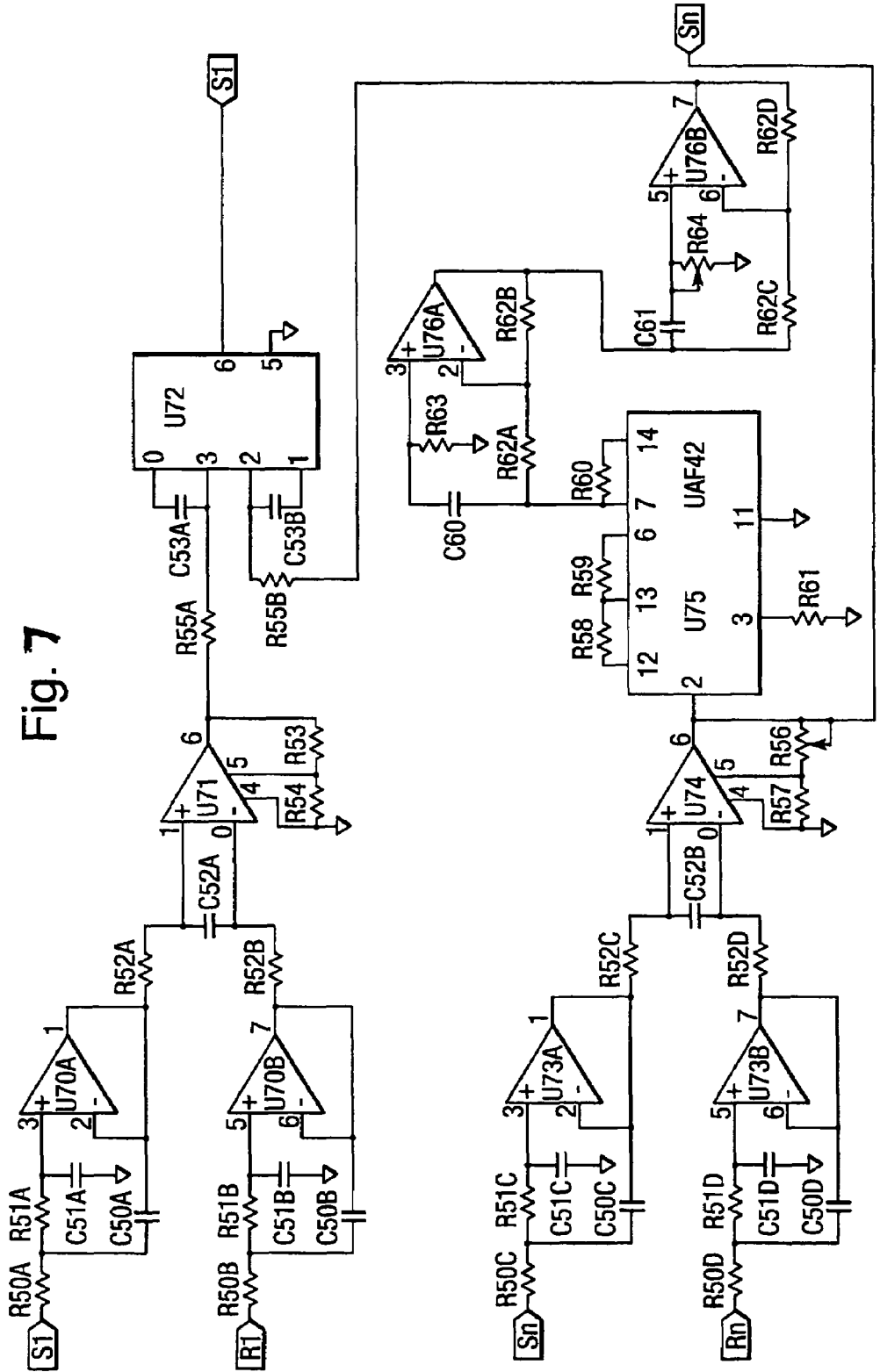
FIGS. 7 and 8 show intermediate circuitry for processing the front end circuitry of FIG. 6.

FIG. 7 shows more of the circuitry enclosed in the shielded amplifier enclosure connected to the outputs of the circuitry shown in FIG. 6 for processing the outputs of the circuitry thereof.

Figure 8:
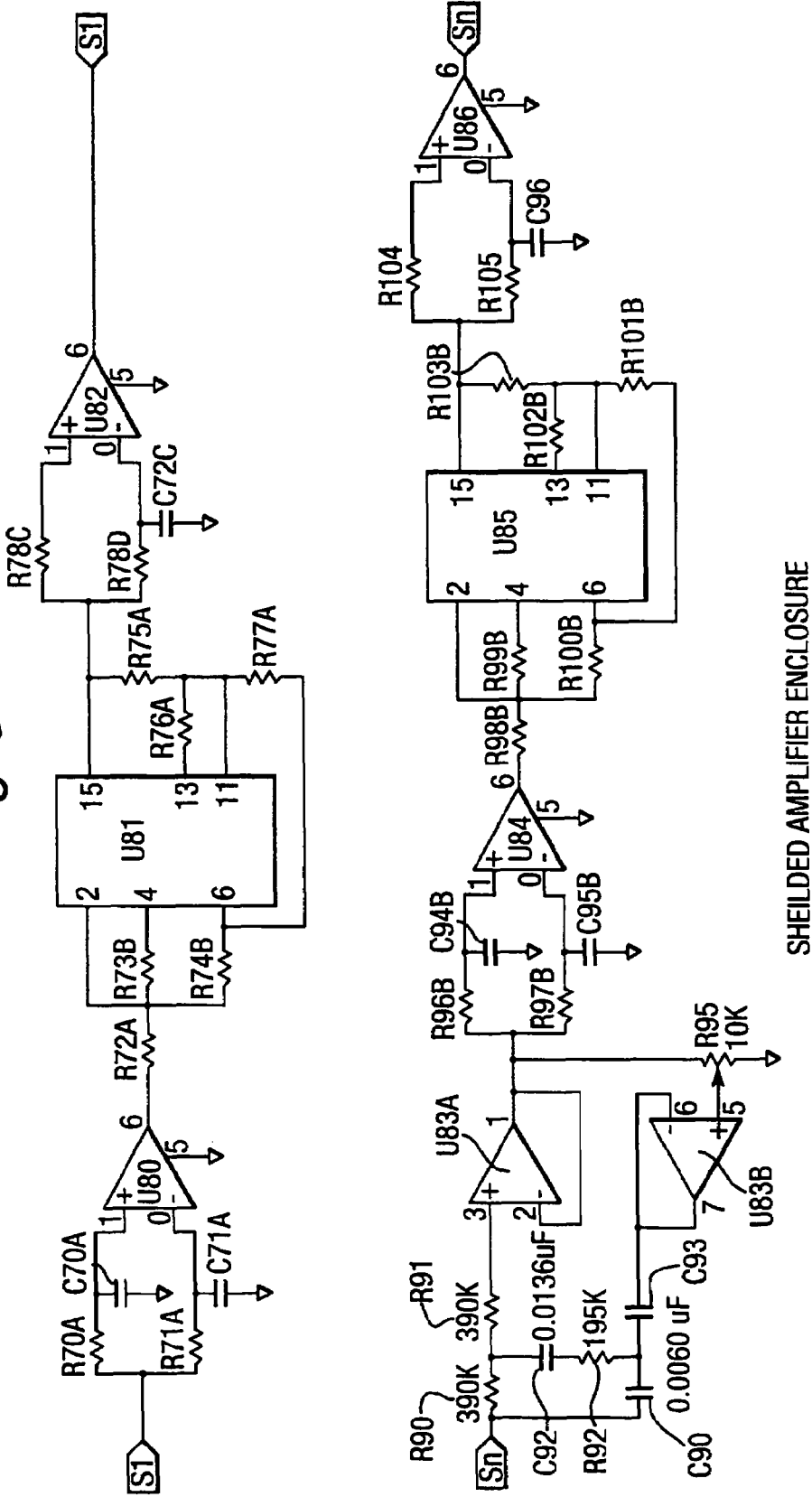

The scalp signal S1 obtained from the output of the amplifier U30A of FIG. 8 is applied to the first terminal of a resistor R50A. The second terminal of the resistor R50A is connected to the first terminal of a resistor R51A and also to the first terminal of a capacitor C50A. The second terminal of the resistor R51A is connected to the first terminal of the capacitor C51A and to the non-inverting input of an amplifier U70A. The second terminal of the capacitor C51A is connected to circuit ground and the second terminal of the capacitor C50A is connected to the inverting input of the operational amplifier U70A and also to the output of the operational amplifier U70A.

Similarly, the reference signal R1 (which is obtained from the output of the operational amplifier U40A in FIG. 6) is applied to the first terminal of a resistor R50B. The second terminal of the resistor R50B is connected to the first terminal of a resistor R51B and to the first terminal of a capacitor C50B. The second terminal of the resistor R51B is connected to the first terminal of a capacitor C51B and to the non-inverting input of an operational amplifier U70B. The second terminal of the capacitor C51B is connected to circuit ground and the second terminal of the capacitor C50B is connected to the inverting input of the operational amplifier U70B and to the output of the operational amplifier U70B.

The output of the operational amplifier U70A is connected to the first terminal of a resistor R52A. The second terminal of the resistor R52A is connected to the non-inverting input of an operational amplifier U71. Similarly, the output of the operational amplifier U70B is connected to a first terminal of a resistor R52B and the second terminal of the resistor R52B is connected to the inverting input of the operational amplifier U71. A capacitor C52A is connected between the inverting and non-inverting inputs of the operational amplifier U71.

The output of the operational amplifier U71 is connected to the first terminal of a resistor R53. The second terminal of the resistor R53 is connected to the first terminal of a resistor R54 and to the gain-setting terminal of the operational amplifier U71. The second terminal of the resistor R54 is connected to circuit ground.

The output of the operational amplifier U71 is also connected to the first terminal of a resistor R55A. The second terminal of the resistor R55A is connected to the first terminal of a capacitor C53A and to the non-inverting input of an operational amplifier U72. The second terminal of the capacitor C53A is connected to a frequency control input of the operational amplifier U72.

Similarly, a measurement signal Sn obtained from the output of the amplifier U30B in the circuit of FIG. 6 is applied to the first terminal of a resistor R50C. The second terminal of the resistor R50C is connected to a first terminal of a resistor R51C and to the first terminal of a capacitor C50C. The second terminal of the resistor R51C is connected to a first terminal of a capacitor C51C and to the non-inverting input of an operational amplifier U73A. The second terminal of the capacitor C50C is connected to the inverting input of the operational amplifier U73A and to the output of the operational amplifier U73A.

The corresponding reference signal obtained from the output of the operational amplifier U40B in the circuit of FIG. 6 is connected to the first terminal of a resistor R50D, the second terminal of the resistor R50D being connected to the first terminal of a resistor R51D and to the first terminal of a capacitor C50D. The second terminal of the resistor R51D is connected to the first terminal of a capacitor C51D and to the non-inverting input of an operational amplifier U73B. The second terminal of the capacitor C51D is connected to circuit ground.

The second terminal of the capacitor C50D is connected to the inverting input of the operational amplifier U73B and to the output of the operational amplifier U73B.

The output of the operational amplifier U73A is connected to a first terminal of a resistor R52C and the second terminal of the resistor R52C is connected to the non-inverting input of a further operational amplifier U74. In the reference line, the output of the operational amplifier U73B is connected to a first terminal of a resistor R52D and the second terminal of the resistor R52D is connected to the inverting input of the operational amplifier U74. The capacitor 52B is connected between the inputs of the operational amplifier U74.

The output of the operational amplifier U74 is connected to a first terminal of a variable resistor R56, the second terminal of the variable resistor R56 being connected to the first terminal of a resistor R57 and also to a gain setting input of the amplifier U74. The second terminal of the resistor R57 is connected to circuit ground. The output of the operational amplifier U74 is also connected to the input of a filter integrated circuit U75 which may be set to 50 or 60 Hz.

The centre frequency of the filter U75 is determined by a number of resistors R58, R59, R60 and 61 connected to the appropriate pins of the filter unit U75. The output from the filter unit U75 is connected to the first terminal of a capacitor C60 and to the first terminal of a resistor R62A. The second terminal of the capacitor C60 is connected to the first terminal of a resistor R63 and to the non-inverting input of an operational amplifier U76A. The second terminal of the resistor R62A is connected to the non-inverting input of the operational amplifier U76A and also to the first terminal of a resistor R62B. The second terminal of the resistor R62B is connected to the output of the operational amplifier U76A, to the first terminal of a capacitor C61 and to the first terminal of a resistor R62C. The second terminal of the capacitor C61 is connected to the first terminal of a variable resistor R64 and to the non-inverting input of an operational amplifier U76B. The second terminal of the resistor R62C is connected to the inverting input of the operational amplifier U76B and to the first terminal of a resistor R62D. The second terminal of the resistor R62D is connected to the output of the operational amplifier U76B. The output of the operational amplifier U76B is also connected to the first terminal of a resistor R55B, the second terminal of the resistor R55B being connected to the inverting input of the operational amplifier U72 and to the first terminal of the capacitor C53B. The second terminal of the capacitor C53B is connected to a frequency correction input of the operational amplifier U72.

In FIG. 7, the signal and reference signals are filtered by second order Bessel filters constructed around U70 and U73, which are dual operational amplifiers of the same types as U30 and U40 of FIG. 6. The Bessel filters are low pass, with a cutoff (−3 dB) typically of 145 Hz. Resistors R50 and R51 are 6650 ohms, capacitors C51 are 0.12 µF and capacitors C50 are 0.22 µF for 145 Hz cutoff. The filters must be closely matched in each signal-reference pair to maintain high noise rejection at the differential amplifier; this is achieved by closely matching the filter components preferably to within 0.1% tolerance, or to a maximum of 1% tolerance.

Following the Bessel filters, a differential mode to common mode filter composed of resistors R52 and capacitors C52 (600 ohms and 1.0 µF respectively for a cutoff frequency of 133 Hz) is placed at the input of a wide bandwidth differential amplifier (U71 and U74 in FIG. 7) such as Analog Devices™ AD8129 or similar. The reference loop signal is subtracted at this stage, with an equivalent third order low pass filter of 100 Hz cutoff formed by the combination of filters and differential amplifier. Although low pass filtering is advantageous for minimizing interference, the signal and reference loops must be well-matched in order to minimize interference within the signal bandwidth, 100 Hz in this case.

The gain for the differential amplifier is typically set at 12.5. In FIG. 7, resistors R54 and R53 (221 ohms and 2.55K ohms respectively) set the gain for the signal channels. Channel n, connected to a neutral location on the body near the physiological signals of interest (such as the earlobe or behind the ear for EEG) is used for powerline interference reduction. After rf and magnetically induced interference is filtered and subtracted from channel n, the remaining signal (composed primarily of 50/60 Hz voltages capacitively coupled to the body from the power mains) is subtracted from the EEG signal. Therefore, channel n must be closely matched at 50/60 Hz to the EEG channels, and an adjustable gain control at differential amplifier U74 in FIG. 7 enables matching the gain of channel n to the other channels. The gain range for U74 is set by R57 at 221 ohms, and R56, a 2490 ohms resistor in series with a 100 ohms potentiometer. For maximum powerline rejection, a variable gain control may be added to each EEG channel for individual adjustment, such as replacing R53 with a 2490 ohms resistor in series with a 100 ohms potentiometer.

Since the signal on channel n is subtracted from the other signal channels, any residual interference appearing on channel n from sources other than 50/60 Hz powerline voltages will appear on the signal channels if it is not matched to the interference on each signal channel. Precise matching of residual interference across channels is not expected, so a means of minimizing any signal other than powerline noise appearing on channel n is necessary.

One method, shown in FIG. 7, is to bandpass filter channel n with a Texas Instruments™ UAF42 filter IC (U75) set at 50 or 60 Hz. For a center frequency of 60 Hz, Q equal to 30, and bandpass gain of 1, R58 is set to 5.49K ohms, R59 and R60 are 834K ohms, and R61 is 487 ohms. Phase adjustment is necessary after filtering to precisely match the phase of the 50/60 Hz signal remaining on channel n to the other signal channels. In FIG. 7, this is implemented with two all pass filter circuits constructed around dual operational amplifier U75 (Texas Instruments TL072 or similar). For 90 degrees of phase shift at 60 Hz, capacitors C60 and C61 are set to 1 µF. Resistor R63 is 265K ohms and resistor R64 is a combination of 261K ohms in series with a 10K ohms potentiometer for phase adjustment. Resistors R62 are 100K ohms. Alternatively, R64 may be replaced with a digitally controlled potentiometer as described above for adjusting amplifier gains, in order to adjust phase shift by programmed means.

An alternative approach (not shown) is to use a bandpass filter with lower Q to allow a passband of 50 to 60 Hz, and follow with a phase locked loop to lock onto the powerline noise. The output of the phase locked loop is phase adjusted and the gain may be trimmed to match the powerline interference appearing on the signal channels. The filtered and phase adjusted powerline interference signal on channel n is subtracted from the signal channels using a differential amplifier (U72 in FIG. 14, Analog Devices AD620 or similar). Resistors R55 (1K ohms) and capacitors C51 (150 pF) filter high frequency noise appearing at the output of the wide bandwidth differential amplifier U71, and match the inputs at U72.

In FIG. 8, the main stages of signal amplification and additional filtering are shown.

Signal S1 obtained from the output of the differential amplifier U72 in the circuit of FIG. 7 is applied to the first terminals of further resistors R70A and R71A as shown in FIG. 8. The second terminal of the resistor R70A is connected to the first terminal of a capacitor C70A and to the non-inverting input of a further operational amplifier U80. The second terminal of the resistor R71A is connected to the first terminal of a capacitor C71A and to the inverting input of the operational amplifier U80. The second terminals of the capacitors C70A and C71A are taken to circuit ground. The output of the operational amplifier U80 is taken to a first terminal of a resistor R72A and the second terminal of the resistor R72A is connected to the first terminal of a resistor R73B and to the first terminal of a resistor R74B as well as to the input of a filter U81.

The second terminals of the resistors R73B and R74B are taken to the filter control terminals of the filter U81. The output of the filter U81 is connected to a first terminal of a resistor R75A and the second terminal of the resistor R75A is connected to the first terminals of resistors R76A and R77A. The second terminal of the resistor R77A is taken to a filter control terminal of the filter U81. The second terminal of the resistor R76A is connected to a filter control terminal of the filter U81. The output of the filter U81 is connected to a second terminal of a resistor R75A and to the first terminal of a resistor R78C as well as to a first terminal of a resistor R78D. The second terminal of resistor R78C is connected to the non-inverting input of an operational amplifier U82. The second terminal of the resistor R78D is connected to the first terminal of a capacitor C72C and to the inverting input of the operational amplifier U82. The second terminal of the capacitor C72C is taken to circuit ground. The output signal S1 with reduced interference is obtained from the output of the operational amplifier U82.

The ground signal Sn taken from the output of the operational amplifier U74 in the circuit of FIG. 7 is connected, as shown in the circuit of FIG. 8, to the first terminal of a resistor R90 and to the first terminal of a capacitor C90. The second terminal of the resistor R90 is connected to the first terminal of resistor R91 as well as to the first terminal of a capacitor C92. The second terminal of capacitor C90 is connected to the first terminal of a resistor R92 and to the first terminal of a capacitor C93. The second terminal of the capacitor C92 is connected to the second terminal of the resistor R92. The second terminal of the resistor R91 is connected to the non-inverting input of an operational amplifier U83A. The inverting input of the operational amplifier U83A is connected to the output of the operational amplifier U83A.

The second terminal of the capacitor C93 is connected to the inverting input of a further operational amplifier U83B and to the output of the operational amplifier U83B. The non-inverting input of the operational amplifier U83B is connected to the slider of a variable resistor R95. The first terminal of the resistor R95 is connected to the output of the operational amplifier U83A and the second terminal of the resistor R95 is connected to circuit ground.

The output of the operational amplifier U83A is further connected to the first terminals of two resistors R96B and R97B. The second terminal of the resistor R96B is connected to the first terminal of a capacitor C94B and to the non-inverting input of a further operational amplifier U84. The second terminal of the resistor R97B is connected to the first terminal of a capacitor C95B and to the inverting input of the operational amplifier U84. The second terminals of the capacitors C94B and C95B are connected to circuit ground.

The output of the operational amplifier U84 is connected to the first terminal of a resistor R98B. The second terminal of the resistor R98B is connected to the input of a filter unit U85 and to the first terminals of two resistors R99B and R100B. The second terminals of the resistors R99B and R100B are connected to the filter control terminals of the filter unit U85.

The second terminal of the resistor R100B is connected to the first terminal of a resistor R101B and the second terminal of the resistor R101B is connected to a filter control terminal of the filter unit U85 and to the first terminals of two resistors R102B and R103. The second terminal of the resistor R102B is connected to the filter control terminal of the filter unit U85 and the output of the filter unit U85 is connected to a second terminal of the resistor R103B and to the first terminals of two resistors R104 and R105. The second terminal of the resistor R104 is taken to the non-inverting input of an operational amplifier U86 and the second terminal of the resistor R105 is taken to the first terminal of a capacitor C96 and to the inverting input of the operational amplifier U86. The second terminal of the capacitor C96B is taken to circuit ground. The ear reference signal with the 50/60 Hz interference removed is obtainable from the output of the operational amplifier U86.

At the input to U80 (differential amplifier such as Analog Devices™ AD627), the signal channel is high pass filtered to remove DC offsets appearing at the electrode interface to the body. Typical values for components are: R70, 39.2K ohms, R71, 1.6M ohms, C60, 0.01 µF, and C61 0.1 µF. Gain for this stage is set at 10. Following is a fourth order Butterworth low pass filter with a cutoff frequency of 256 Hz. This may be implemented using a Linear Devices™ LTC1563-2 filter (U81 in FIG. 15) with resistors R72 through R77 set to 10M ohms. Additional gain of 50 and DC offset filtering is added at U82 and U86 (AD627 typically) with R71, R78, R97, R104 and R105 set to 1.6M ohms and C71, C72, C95, and C96 at 0.1 µF.

Although all channels have the same amplification and filtering as outlined above, channel n has an additional filter as shown in FIG. 8. Since channel n is the ear reference channel, the primary signal appearing on this channel is a large 50/60 Hz signal. As previously described, this signal is subtracted from the signal channels to remove powerline interference. However, in some applications, it may be necessary to observe channel n in order to adjust the reference loop gain for minimizing rf and magnetically induced interference. Therefore, the original channel n signal appearing at the output of U74 in FIG. 7 is routed through a 50 or 60 Hz notch filter in FIG. 8 before amplification and digitization for display. A 60 Hz notch filter is built around operational amplifier U83 (Texas Instruments™ TL072 or similar) using component values shown in FIG. 8, resulting in approximately 45 dB of rejection at 60 Hz, sufficient for displaying channel n without excess powerline noise swamping the trace.

This circuitry enables the powerline interference component to be filtered out and the measurement signals further processed downstream, e.g. using software, to sequentially filter out other interference components.

Figure 9:
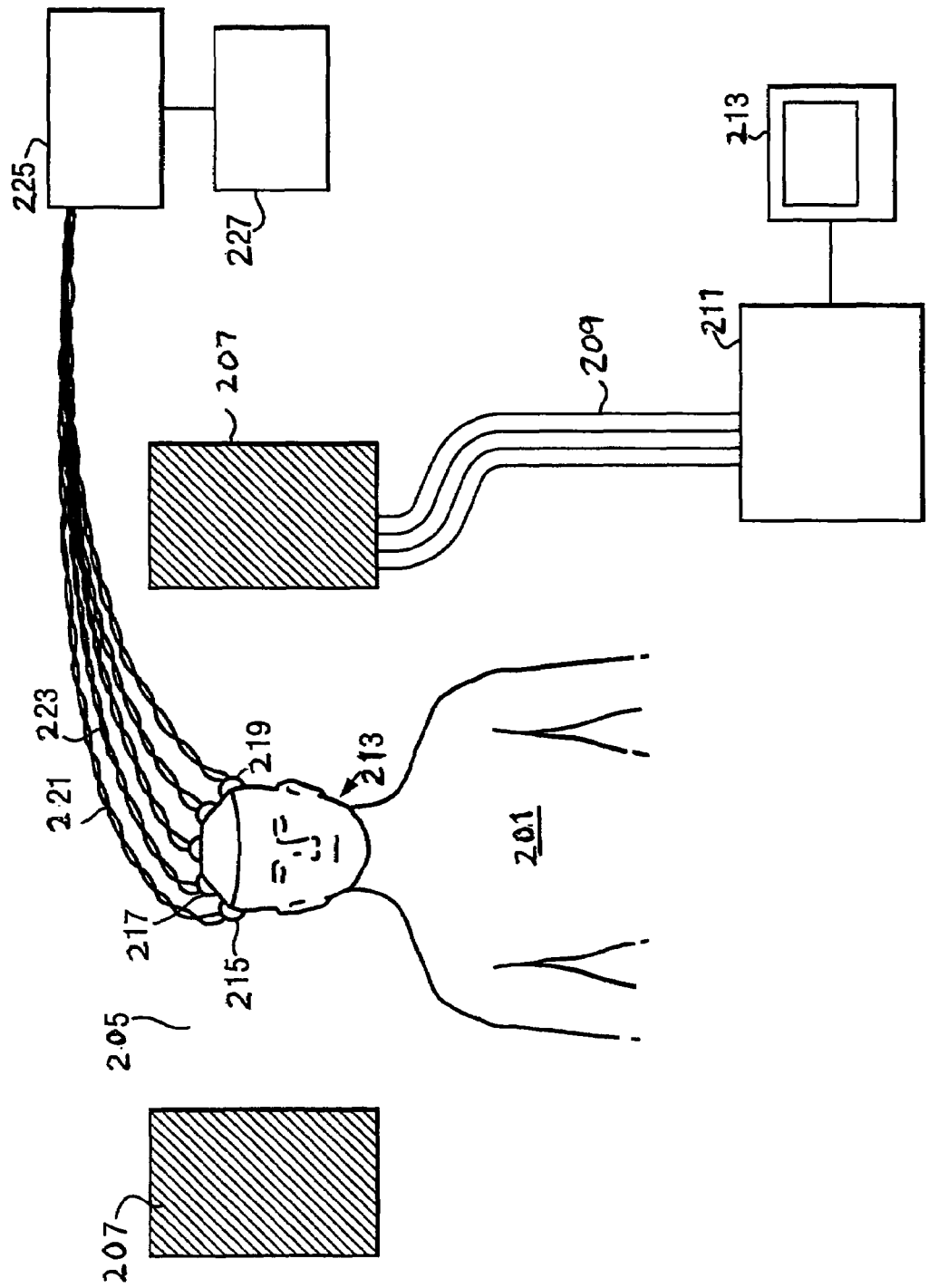
FIG. 9 shows how an electrode cap according to either embodiment shown in FIGS. 1-5 may be used with electronic circuitry such as in any of FIG. 6-8 in combination with an MRI or a fMRI unit.

FIG. 9 shows a combined fMRI and EEG system in which either of the electrode caps of FIGS. 1-5 and the electronic circuit of FIGS. 6-8 may be employed.

As shown in FIG. 9, a subject 201 is arranged with the subject's head 203 located within the bore 105 of an fMRI coil unit 207 which carries magnetic field windings and rf coils. These coils and windings are energised via a multiplicity of wiring connections 109 etc which connect the coil unit 207 to operational circuitry 211. The operational circuitry unit is connected to a memory and display unit 213 whereby the MRI scans can be stored, displayed and printed at will.

A plurality of electrodes 215, 217, 219 etc for obtaining EEG signals are attached to the scalp of the subject 201. As will be explained in more detail hereinbelow, one of these electrodes 219 is a reference node. Signals from the electrodes 215, 217, 219 etc are conveyed by wires 221, 223 etc to an EEG control unit 225 which is connected to a recorder 227 situated outside the MRI room.

The combined fMRI/EEG arrangement may be considered to apply to any specific embodiment of EEG processing circuitry described hereinbelow.

In a worked embodiment, the MRI system used for obtaining data presented in more detail hereinbelow was the Siemens Allegra™ (3.0T)-MR6.

The Siemens Allegra™ 3T is a head-only magnet. It has the necessary hardware and software to perform basic and clinical scans. Gradient hardware consists of a 36 cm I.D. asymmetric gradient coil capable of imaging at 60 mT/m with slew rates in excess of 600 T/m/s at a duty cycle of 70% allowing single shot echoplanar imaging (EPI) at a sustained rate of 14 images/second. The system has a 15 kW RF amplifier, and 8 RF preamp channels for this system supports the Syngo™ software on a Windows™ NT platform.

The EPI regime employed 1 to 13 gradient switching pulses (images) per second. Gradient strength: 20-35 mT/m, max 40 mT/m; Slew rate: 400 mT/m/msec. Pulse width: 0.32-0.64 msec, oscillating between positive and negative gradients. Rf pulse freq: 126 MHz, frequency modulated for slice position.

The conventional sequence used for fMRI is multi-slice echo planar imaging. In this, the largest gradient is applied as a bi-polar square wave, which is often modified to be more trapezoidal or sinusoidal in form (to smooth the edges). Typically for one image this is applied for 20-100 ms with a fundamental frequency of 2 to 0.5 kHz. One of the other two gradients is usually applied as a series of smaller pulses (100 µs duration typical) at the zero crossings of the big switched gradient, whilst the third (slice select) gradient is generally just applied at the beginning of the sequence as a bi-polar square pulse, typically lasting 3-5 ms. The rf is usually just applied at the same time as the slice select gradient.

The present invention is not limited by the described embodiments but modifications of these embodiments, as well as other embodiments all within the spirit and scope of the invention disclosed and taught herein, for example as defined in the appended claims, are hereby made possible.

The invention claimed is:

1. An electrode cap for obtaining EPM signals from a head of a subject, the cap comprising:
   (i) an insulating layer for positioning adjacent to the head of the subject;
   (ii) an electrically conductive layer situated above the insulating layer so that in use, it is separated from the head of the subject by the insulating layer; the electrical conductivity of the electrically conductive layer being predominantly due to ionic conductive means;
   (iii) a plurality of measurement signal electrodes extending through the electrically conductive layer and the insulating layer for contacting the head of the subject, the measurement signal electrodes being electrically insulated from the electrically conductive layer; and
   (iv) at least one reference node is electrically connected to the electrically conductive layer;
wherein a plurality of reference nodes is electrically connected to the electrically conductive layer.

2. An electrode cap according to claim 1, wherein the electrically conductive layer comprises an electrically conductive medium having a resistivity of from 0.5 ohm cm to 350 ohm cm.

3. An electrode cap according to claim 1, wherein the electrically conductive layer comprises an electrically conductive medium having a resistivity from 0.01 ohm cm to 1,000 ohm cm.

4. An electrode cap according to claim 1, wherein the electrically conductive medium comprises an aqueous saline solution.

5. An electrode cap according to claim 1, in which the electrically conductive medium is an aqueous electrically conductive gel comprising a thickener selected from polysaccharide gum thickeners, starch and starch derivative thickeners and synthetic polymer thickeners.

6. An electrode cap according to claim 5, further comprising valve means allowing inflation and deflation of the bladder and maintenance of the bladder in an inflated state.

7. An electrode cap according to claim 1, further comprising securing means for securing it to the head of the subject.

8. An electrode cap according to claim 1, wherein the securing means comprises a bladder.

9. An electrode cap according to claim 8, wherein the bladder is in the form of a layer situated above the electrically conductive layer and the insulating layer.

10. An electrode cap according to claim 8, wherein the bladder is adapted to be inflated.

11. An electrode cap according to claim 10, further comprising inflation means for injecting fluid into the bladder.

12. An electrode cap according to claim 8, wherein the bladder contains a plurality of solid pieces and is adapted to be evacuated.

13. An electrode cap according to claim 12, further comprising evacuation means for withdrawing air from the bladder.

14. An electrode cap according to claim 12, further comprising valve means allowing withdrawal or ingress of air from the bladder and maintenance of the bladder in a reduced pressure state.

15. An electrode cap according to claim 1, wherein the number of said reference nodes is substantially the same as the number of said measurement signal electrodes.

16. An electrode cap according to claim 1, wherein each measurement signal electrode or group signal electrodes has a corresponding respective reference node in close physical proximity thereto.

17. An electrode cap according to claim 1, wherein said cap further supports one or more ground electrodes presented for contacting the skin of the subject in use, the cap further comprising third connection means for independent electrical connection to each of said ground electrode or electrodes.

18. An electrode cap according to claim 1, wherein the cap supports a single ground electrode.

19. An electrode cap according to claim 1, further comprising a compensation signal electrode extending through the electrically conductive layer and the insulating layer for contacting the subject in a compensation signal position, the compensation signal electrode being electrically insulated from the electrically conductive layer.

20. An electrode cap according to claim 19, wherein a respective reference node with its own independent electrical connection is provided for the ground electrode and the compensation signal electrode.

21. An electrode cap according to claim 1, wherein said cap is substantially entirely flexible.

22. An electrode cap according to claim 1, wherein part of said cap is substantially rigid, the conductive layer being flexible.

23. An electronic apparatus comprising an electrode cap according to claim 1 and an electronic circuit, the electronic circuit comprising:
  (a) a plurality of measurement inputs, each connected to a respective one of the measurement signal electrodes; and
  (b) a plurality of reference signal inputs, each connected to a respective one or more of the reference nodes;
said electronic apparatus further comprising subtraction means for subtracting an interference signal from each respective reference signal input from an interference signal from a corresponding measurement signal input or from each respective measurement signal input in a group of measurement signal inputs.

24. An electronic apparatus according to claim 23, wherein the interference comprises a plurality of interference components, the electronic circuit further comprising:
  (a) at least one primary signal processing unit, the or each primary signal processing unit having a respective measurement signal input for receiving a respective one of said measurement signal or signals and the or each primary signal processing unit comprising a plurality of interference reduction modules; and
  (b) a respective compensation signal component input for each interference reduction module.

25. An electronic apparatus according to claim 23, further comprising:
  (a) a compensation signal processing unit having a compensation signal input and comprising means for deriving from a compensation signal, a plurality of compensation signal components each of which is related to a respective one or more of the interference components; and
  (b) the compensation signal processing unit also having a respective compensation signal component output for each compensation signal component, each said output being respectively connected to one of the compensation signal component inputs.

26. An electronic apparatus according to claim 25, wherein in each primary signal processing unit, the interference reduction modules are arranged in series.

27. An electronic apparatus according to claim 25, wherein in each primary signal processing unit, respective interference reduction modules are provided for reduction of at least two of rf interference, magnetic field switching interference, mains power interference, eyeblink artifact interference and ballistocardiogram interference, respectively.

28. A combined measurement apparatus comprising an MRI or TMS unit and an EPM system which comprises an electronic apparatus according to claim 1.

29. A combined apparatus according to claim 28, wherein the MRI unit is adapted for fMRI.

30. A combined apparatus according to claim 28, wherein the EPM system is selected from systems for effecting one or more of EEG, EDG, EMG, EOG, ERG and GSR.

31. An electrode cap according to claim 30, wherein the bladder means is in the form of a layer situated above the electrode support means.

32. An electrode cap according to claim 1, the cap comprising an electrode support means comprising said insulating layer and said electrically conductive layer, said plurality of electrodes being supported on said electrode support means to allow said electrodes to contact the head and bladder means for securing said electrodes relative to the head.

33. An electrode cap according to claim 32, wherein the bladder means is adapted to be inflated.

34. An electrode cap according to claim 33, further comprising inflation means for injecting fluid into the bladder means.

35. An electrode cap according to claim 32, further comprising valve means allowing inflation and deflation of the bladder means and maintenance of the bladder means in an inflated state.

36. An electrode cap according to claim 32, wherein the bladder means contains a plurality of solid pieces and is adapted to be evacuated.

37. An electrode cap according to claim 36, further comprising evacuation means for withdrawing air from the bladder means.

38. An electrode cap according to claim 36, further comprising valve means for allowing withdrawal or ingress of air from the bladder means and maintenance of the bladder means in a reduced pressure state.

* * * * *